US011850293B2

(12) United States Patent
Hamersky et al.

(10) Patent No.: US 11,850,293 B2
(45) Date of Patent: Dec. 26, 2023

(54) ACTIVE AGENT-CONTAINING MATRIX PARTICLES AND PROCESSES FOR MAKING SAME

(71) Applicant: The Procter & Gamble Company, Cincinnati, OH (US)

(72) Inventors: Mark William Hamersky, Cincinnati, OH (US); Stephen Robert Glassmeyer, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/575,437

(22) Filed: Sep. 19, 2019

(65) Prior Publication Data

US 2020/0093711 A1 Mar. 26, 2020

Related U.S. Application Data

(60) Provisional application No. 62/881,965, filed on Aug. 2, 2019, provisional application No. 62/734,473, filed on Sep. 21, 2018.

(51) Int. Cl.
| | |
|---|---|
| *A61K 8/02* | (2006.01) |
| *A61K 8/898* | (2006.01) |
| *A61Q 13/00* | (2006.01) |
| *C11D 3/37* | (2006.01) |
| *C11D 3/50* | (2006.01) |
| *C11D 17/04* | (2006.01) |
| *C11D 3/12* | (2006.01) |
| *C11D 11/00* | (2006.01) |

(52) U.S. Cl.
CPC ............ *A61K 8/0283* (2013.01); *A61K 8/027* (2013.01); *A61K 8/0275* (2013.01); *A61K 8/0279* (2013.01); *A61K 8/898* (2013.01); *A61Q 13/00* (2013.01); *C11D 3/124* (2013.01); *C11D 3/3742* (2013.01); *C11D 3/3753* (2013.01); *C11D 3/3776* (2013.01); *C11D 3/505* (2013.01); *C11D 11/0017* (2013.01); *C11D 17/044* (2013.01)

(58) Field of Classification Search
CPC ............ A61K 2800/10; A61K 2800/56; A61K 8/027; A61K 8/0275; A61K 8/0279; A61K 8/0283; A61K 8/8129; A61K 8/898; A61Q 13/00; A61Q 19/00; C11D 11/0017; C11D 17/044; C11D 17/06; C11D 3/124; C11D 3/3742; C11D 3/3753; C11D 3/3776; C11D 3/505
See application file for complete search history.

(56) References Cited

U.S. PATENT DOCUMENTS

| | | | | |
|---|---|---|---|---|
| 3,121,249 | A | * | 2/1964 | Affleck ............... C11D 17/049 510/237 |
| 6,313,080 | B1 | * | 11/2001 | Boskamp ............... C11D 3/001 510/330 |
| 2003/0199412 | A1 | | 10/2003 | Gupta |
| 2005/0075261 | A1 | * | 4/2005 | Baeck .................... C11D 3/222 510/400 |
| 2005/0203215 | A1 | * | 9/2005 | Ugazio ................ A61K 8/0279 523/218 |
| 2011/0182956 | A1 | | 7/2011 | Glenn, Jr. et al. |
| 2013/0036559 | A1 | * | 2/2013 | Saveyn ................ C11D 3/3773 206/576 |
| 2015/0164117 | A1 | * | 6/2015 | Kaplan ................ A61K 8/0208 424/401 |
| 2015/0313807 | A1 | | 11/2015 | Lynch et al. |

FOREIGN PATENT DOCUMENTS

| | | | |
|---|---|---|---|
| EP | 2865423 A2 | 4/2015 | |
| GB | 2140820 A * | 12/1984 | ............ C11D 3/126 |
| JP | 3638645 B2 * | 4/2005 | |
| WO | 2014012099 A1 | 1/2014 | |
| WO | 2018140304 A1 | 8/2018 | |

OTHER PUBLICATIONS

English machine translation of JP-3638645-B2 made on Jun. 5, 2020. (Year: 2020).*
International Search Report and Written Opinion; Application Ser. No. PCT/US2019/051812; dated Nov. 11, 2019,11 pages.

* cited by examiner

*Primary Examiner* — Michael B. Pallay
(74) *Attorney, Agent, or Firm* — James E. Oehlenschlager; C. Brant Cook

(57) ABSTRACT

Matrix particles containing one or more matrix materials and one or more hydrophobic active agents, agglomerated particles made therefrom, fibrous structures containing such matrix particles and/or agglomerated particles, and processes for making same are provided.

17 Claims, 7 Drawing Sheets

ACTIVE AGENT-CONTAINING MATRIX PARTICLES AND PROCESSES FOR MAKING SAME

FIELD OF THE INVENTION

The present invention relates to particles comprising hydrophobic active agents (a hydrophobic active agent-containing particle), and more particularly to matrix particles comprising one or more hydrophobic active agent (also may be referred to as a hydrophobic benefit agent), even more particularly to water-soluble matrix particles comprising one or more hydrophobic active agent, an agglomerated particle (agglomerate) comprising one or more, for example a plurality, of matrix particles, more particularly a water-soluble or at least partially water-soluble agglomerated particle comprising such matrix particles, fibrous structures, more particularly to water-soluble fibrous structures comprising one or more matrix particles, for example one or more water-soluble, hydrophobic active agent-containing matrix particles and/or agglomerated particles comprising such matrix particles, fibrous structure products made therefrom, and processes for making same.

BACKGROUND OF THE INVENTION

Particles comprising active agents are known in the art. However, such known particles exhibit negatives, such as dissolution negatives, leakage, contamination, and release issues that make them unsuitable for various applications.

For example, known encapsulated perfumes employ crosslinked starches as their shell materials and/or "encapsulate materials" that form a shell around a perfume core. The choice of crosslinking the starch and the level of crosslinking promotes low leakage rates of the perfumes from the encapsulate. But since the starch is crosslinked, the encapsulates never fully dissolve, but rather swell when in contact with water and therefore release the perfume, very slowly.

Another known particle comprising active agents such as perfumes and/or silicone are include pastilles and/or prills, which are formed by melting a carrier material, rather than dissolving the carrier material in water. The neat melted carrier material (no added free water), for example melted polyethylene glycol, is mixed with a neat active agent (rather than for example an aqueous emulsion of perfume or silicone), for example perfume or silicone, and then cooled to form solid, nonporous droplets, such that the active agents are present in the continuous carrier material, not within pores present in the carrier material.

While the prior art particles have provided perfume delivery, albeit slowly, such prior art particles (encapsulates) are not suitable for delivering other hydrophobic active agents, for example silicones, such as terminal aminosilicones. In the case of silicones, the potential for leakage is significantly lower than is present for perfumes because the viscosity of the silicones is significantly higher than the viscosity of the perfumes. Further, with the silicones, it is desirable that the matrix materials of the matrix particles fully dissolve to release all of the silicones present in the particles.

One problem with such known particles is the full release of active agents, such as hydrophobic active agents, when wet, such as when exposed to water during use, but maintaining low leakage when dry, for example prior to use by a consumer.

There is a need for a particle, for example a matrix particle, comprising a hydrophobic active agent that overcomes the negatives associated with known particles comprising hydrophobic active agents such as silicones, for example terminal aminosilicones, making such particles, for example such matrix particles, suitable for inclusion into fibrous structures, for example water-soluble fibrous structures.

SUMMARY OF THE INVENTION

The present invention fulfills the need described above by providing a matrix particle comprising one or more matrix materials and one or more hydrophobic active agents, agglomerates comprising such matrix particles, fibrous structures comprising one or more matrix particles and/or one or more agglomerates, and processes for making same.

One solution to the problem described above is to makes and/or provide a matrix particle comprising one or more matrix materials in the form of a porous structure and/or that forms a porous structure comprising a plurality of pores, wherein one or more hydrophobic active agents are present within one or more of the pores, for example such that that at least one of the hydrophobic active agents is released from the matrix particle upon the matrix particle contacting water, for example when the matrix particle is exposed to conditions of intended use, such as when the matrix particle is exposed to water during shampooing of hair, washing of clothes, washing of dishes, and the like, and such that the matrix particle exhibits low to no leakage of the hydrophobic active agent when dry, for example before being exposed to water, such as before use by a consumer; an agglomerate comprising one or more of such matrix particles, and/or a fibrous structure, for example a water-soluble fibrous structure, comprising one or more such matrix particles and/or agglomerates.

In one example of the present invention, a matrix particle comprising one or more matrix materials, for example one or more water-soluble matrix materials, and one or more hydrophobic active agents is provided.

In another example of the present invention, a matrix particle, for example a water-soluble matrix particle, comprising one or more matrix materials in the form of a porous structure comprising a plurality of pores, wherein one or more hydrophobic active agents are present within one or more of the pores, for example a plurality of pores, such as all of the pores and/or randomly present in a plurality of pores, is provided.

In even another example, at least one of the one or more hydrophobic active agents within the matrix particle is released from the matrix particle upon the matrix particle and/or one or more matrix material contacting a polar solvent, for example water, and/or upon dissolution of at least a portion or the entire matrix particle and/or one or more, for example all of the matrix materials, is provided.

In another example of the present invention, an agglomerated particle comprising a two or more and/or a plurality of matrix particles, for example where the matrix particles are bound together to form the agglomerate, is provided.

In another example of the present invention, a fibrous structure, for example a water-soluble fibrous structure, comprising a plurality of fibrous elements and one or more matrix particles and/or one or more agglomerated particles according to the present invention, is provided.

In another example of the present invention, a fibrous structure, for example a water-soluble fibrous structure, comprising a plurality of fibrous elements comprising one or more active agents that are releasable from the fibrous element when exposed to conditions of intended use and one or more matrix particles and/or agglomerated particles according to the present invention such that when the fibrous structure is exposed to conditions of intended use one or more active agents are released from the fibrous structure, is provided.

In yet another example of the present invention, a fibrous structure, for example a water-soluble fibrous structure, comprising a plurality of water-soluble fibrous elements and one or more matrix particles and/or agglomerated particles according to the present invention, is provided.

In even another example of the present invention, a fibrous structure, for example a water-soluble fibrous structure, comprising a plurality of fibrous elements wherein at least one of the fibrous elements comprises one or more filament-forming materials selected from the group consisting of polyvinyl alcohols, and mixtures thereof, and one or more active agents present within the at least one fibrous element and selected from the group consisting of surfactants, and mixtures thereof, and wherein the fibrous structure comprises one or more matrix particles and/or agglomerated particles according to the present invention, is provided.

In even yet another example of the present invention, a multi-ply fibrous structure, for example a multi-ply water-soluble fibrous structure and/or a multi-ply fibrous structure comprising at least one water-soluble fibrous structure, comprising at least one fibrous structure ply of the present invention and at least a second fibrous structure ply, for example another fibrous structure ply of the present invention, which are associated, for example by an edge seam proximate to the edges of the plies, is provided.

In yet another example of the present invention, a process for making a matrix particle, the process comprising the steps of:
 a. making a solution, for example an aqueous solution, comprising one or more matrix materials (Premix 1), for example by dissolving one or more matrix materials into water;
 b. making or providing an emulsion, for example an aqueous emulsion, comprising one or more hydrophobic active agents (Premix 2);
 c. mixing the solution from (a) and the emulsion from (b) together to form a spray drying mixture; and
 d. spray drying the spray drying mixture to form one or more matrix particles according to the present invention, for example wherein the at least one of the hydrophobic active agents is present within at least one pore present in the porous structure formed by the one or more matrix materials, is provided.

In even yet another example of the present invention, a process for making a matrix particle, the process comprising the steps of:
 a. making a solution, for example an aqueous solution, comprising one or more matrix materials (Premix 1), for example by dissolving one or more matrix materials into water;
 b. adding one or more hydrophobic active agents, for example one or more solid hydrophobic active agents, for example particles, such as silica, to the solution ((Premix 1);
 c. mixing the solution from (a) and the one or more hydrophobic active agents together to form a spray drying mixture; and
 d. spray drying the spray drying mixture to form one or more matrix particles according to the present invention, for example wherein the at least one of the hydrophobic active agents is present within at least one pore present in the porous structure formed by the one or more matrix materials, is provided.

In still another example of the present invention, a process for making an agglomerated particle, the process comprising the steps of:
 a. providing a plurality of matrix particles according to the present invention;
 b. mixing, optionally in the presence of a binder, the plurality of matrix particles together to form one or more agglomerated particles according to the present invention, is provided.

In even another example of the present invention, a method for making a fibrous structure, the method comprising the steps of:
 a. providing a fibrous element-forming composition comprising one or more filament-forming materials;
 b. spinning the fibrous element-forming composition into one or more fibrous elements;
 c. providing one or more matrix particles and/or agglomerated particles according to the present invention; and
 d. associating the one or more matrix particles and/or agglomerated particles with the one or more fibrous elements to form a fibrous structure according to the present invention, for example by commingling the matrix particles and/or agglomerated particles with the fibrous elements and/or layering the matrix particles and/or agglomerated particles by deposing the matrix particles and/or agglomerated particles on a layer of fibrous elements, is provided.

Accordingly, the present invention provides novel matrix particles, novel agglomerated particles, novel fibrous structures comprising such matrix particles and/or agglomerated particles, processes for making such matrix particles, processes for making such agglomerated particles, and processes for making such fibrous structures.

BRIEF DESCRIPTION OF THE DRAWINGS

FIG. 2 is a schematic representation of an example of a process for making a matrix particle according to the present invention;

DETAILED DESCRIPTION OF THE INVENTION

Definitions

Figure 1:
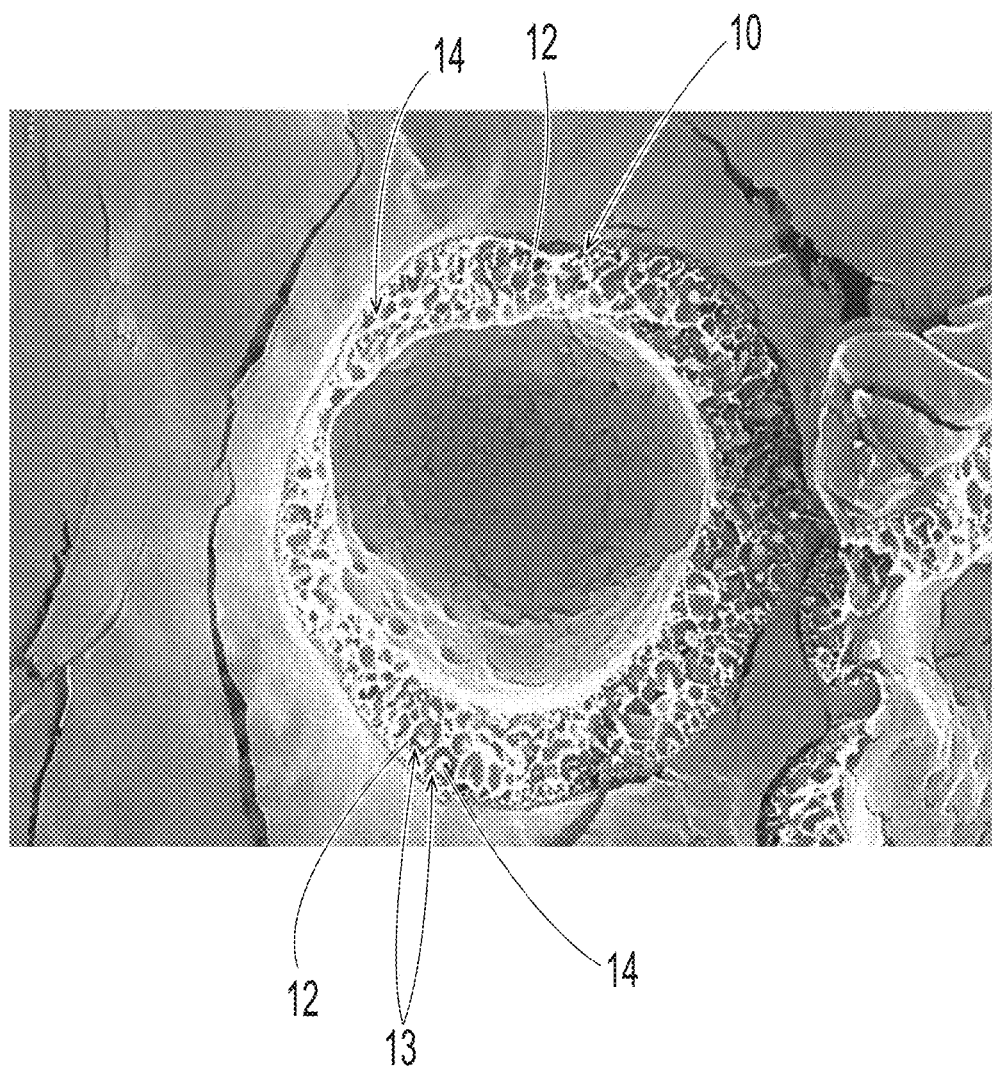
FIG. 1 is a SEM cross-section of an example of a matrix particle according to the present invention.

"Fibrous structure" as used herein means a structure that comprises one or more fibrous elements and one or more particles, for example one or more matrix particles and/or agglomerated particles. In one example, a fibrous structure according to the present invention means an association of fibrous elements and particles, for example matrix particles and/or agglomerated particles, that together form a structure, such as a unitary structure, capable of performing a function.

The fibrous structures of the present invention may be homogeneous or may be layered. If layered, the fibrous structures may comprise at least two and/or at least three and/or at least four and/or at least five layers, for example one or more fibrous element layers, one or more particle (matrix particle and/or agglomerated particle) layers and/or one or more fibrous element/particle mixture layer.

In one example, the fibrous structure is a multi-ply fibrous structure that exhibits a basis weight of less than 5000 g/m$^2$ as measured according to the Basis Weight Test Method described herein.

In one example, the fibrous structure of the present invention is a "unitary fibrous structure."

"Unitary fibrous structure" as used herein is an arrangement comprising one or more particles, for example one or more matrix particles and/or agglomerated particles, and a plurality of two or more and/or three or more fibrous elements that are inter-entangled or otherwise associated with one another to form a fibrous structure. A unitary fibrous structure of the present invention may be one or more plies within a multi-ply fibrous structure. In one example, a unitary fibrous structure of the present invention may comprise three or more different fibrous elements. In another example, a unitary fibrous structure of the present invention may comprise two different fibrous elements, for example a co-formed fibrous structure, upon which a different fibrous element is deposited to form a fibrous structure comprising three or more different fibrous elements.

"Fibrous element" as used herein means an elongate particulate having a length greatly exceeding its average diameter, i.e. a length to average diameter ratio of at least about 10. A fibrous element may be a filament or a fiber. In one example, the fibrous element is a single fibrous element rather than a yarn comprising a plurality of fibrous elements.

The fibrous elements of the present invention may be spun from a filament-forming composition also referred to as fibrous element-forming compositions via suitable spinning process operations, such as meltblowing, spunbonding, electro-spinning, and/or rotary spinning The fibrous elements of the present invention may be monocomponent and/or multicomponent. For example, the fibrous elements may comprise bicomponent fibers and/or filaments. The bicomponent fibers and/or filaments may be in any form, such as side-by-side, core and sheath, islands-in-the-sea and the like.

"Filament" as used herein means an elongate particulate as described above that exhibits a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.).

Filaments are typically considered continuous or substantially continuous in nature. Filaments are relatively longer than fibers. Non-limiting examples of filaments include meltblown and/or spunbond filaments. Non-limiting examples of polymers that can be spun into filaments include natural polymers, such as starch, starch derivatives, cellulose, such as rayon and/or lyocell, and cellulose derivatives, hemicellulose, hemicellulose derivatives, and synthetic polymers including, but not limited to thermoplastic polymer filaments, such as polyesters, nylons, polyolefins such as polypropylene filaments, polyethylene filaments, and biodegradable thermoplastic fibers such as polylactic acid filaments, polyhydroxyalkanoate filaments, polyesteramide filaments and polycaprolactone filaments.

"Fiber" as used herein means an elongate particulate as described above that exhibits a length of less than 5.08 cm (2 in.) and/or less than 3.81 cm (1.5 in.) and/or less than 2.54 cm (1 in.).

Fibers are typically considered discontinuous in nature. Non-limiting examples of fibers include staple fibers produced by spinning a filament or filament tow of the present invention and then cutting the filament or filament tow into segments of less than 5.08 cm (2 in.) thus producing fibers.

In one example, one or more fibers may be formed from a filament of the present invention, such as when the filaments are cut to shorter lengths (such as less than 5.08 cm in length). Thus, in one example, the present invention also includes a fiber made from a filament of the present invention, such as a fiber comprising one or more filament-forming materials and one or more additives, such as active agents. Therefore, references to filament and/or filaments of the present invention herein also include fibers made from such filament and/or filaments unless otherwise noted. Fibers are typically considered discontinuous in nature relative to filaments, which are considered continuous in nature.

"Filament-forming composition" and/or "fibrous element-forming composition" as used herein means a composition that is suitable for making a fibrous element of the present invention such as by meltblowing and/or spunbonding. The filament-forming composition comprises one or more filament-forming materials that exhibit properties that make them suitable for spinning into a fibrous element. In one example, the filament-forming material comprises a polymer. In addition to one or more filament-forming materials, the filament-forming composition may comprise one or more additives, for example one or more active agents. In addition, the filament-forming composition may comprise one or more polar solvents, such as water, into which one or more, for example all, of the filament-forming materials and/or one or more, for example all, of the active agents are dissolved and/or dispersed prior to spinning a fibrous element, such as a filament from the filament-forming composition.

In one example, a filament of the present invention made from a filament-forming composition of the present invention is such that one or more additives, for example one or more active agents, may be present in the filament rather than on the filament, such as a coating composition comprising one or more active agents, which may be the same or different from the active agents in the fibrous elements and/or particles. The total level of filament-forming materials and total level of active agents present in the filament-forming composition may be any suitable amount so long as the fibrous elements of the present invention are produced therefrom.

In one example, one or more additives, such as active agents, may be present in the fibrous element and one or more additional additives, such as active agents, may be present on a surface of the fibrous element. In another example, a fibrous element of the present invention may comprise one or more additives, such as active agents, that are present in the fibrous element when originally made, but then bloom to a surface of the fibrous element prior to and/or when exposed to conditions of intended use of the fibrous element.

"Filament-forming material" as used herein means a material, such as a polymer or monomers capable of producing a polymer that exhibits properties suitable for making a fibrous element. In one example, the filament-forming material comprises one or more substituted polymers such as an anionic, cationic, zwitterionic, and/or nonionic polymer. In another example, the polymer may comprise a hydroxyl polymer, such as a polyvinyl alcohol ("PVOH"), a partially hydrolyzed polyvinyl acetate and/or a polysaccharide, such as starch and/or a starch derivative, such as an ethoxylated starch and/or acid-thinned starch, carboxymethylcellulose, hydroxypropyl cellulose, hydroxyethyl cellulose. In another example, the polymer may comprise polyethylenes and/or terephthalates. In yet another example, the filament-forming material is a polar solvent-soluble material.

"Commingled" and/or "commingling" as used herein means the state or form where particles, for example matrix particles and/or agglomerated particles, are mixed with fibrous elements, for example filaments. The mixture of filaments and particles can be throughout a composite structure or within a plane or a region of the composite structure. In one example, the commingled filaments and particles may form at least a surface of a composite structure. In one example, the particles may be homogeneously dispersed throughout the composite structure and/or plane and/or region of the composite structure. In one example, the particles may be homogeneously distributed throughout the composite structure, which avoids and/or prevents sag and/or free movement and/or migration of the particles within the composite structure to other areas within the composite structure thus resulting in higher concentrated zones of particles and lower concentrated zones or zero concentration zones of particles within the composite structure. In one example, μCT cross-sections of a composite structure can show whether the particles are homogeneously distributed throughout a composite structure.

"Additive" as used herein means any material present in the fibrous element of the present invention that is not a filament-forming material. In one example, an additive comprises an active agent. In another example, an additive comprises a processing aid. In still another example, an additive comprises a filler. In one example, an additive comprises any material present in the fibrous element that its absence from the fibrous element would not result in the fibrous element losing its fibrous element structure, in other words, its absence does not result in the fibrous element losing its solid form. In another example, an additive, for example an active agent, comprises a non-polymer material.

In another example, an additive may comprise a plasticizer for the fibrous element. Non-limiting examples of suitable plasticizers for the present invention include polyols, copolyols, polycarboxylic acids, polyesters and dimethicone copolyols. Examples of useful polyols include, but are not limited to, glycerin, diglycerin, propylene glycol, ethylene glycol, butylene glycol, pentylene glycol, cyclohexane dimethanol, hexanediol, 2,2,4-trimethylpentane-1,3-diol, polyethylene glycol (200-600), pentaerythritol, sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, high fructose corn syrup solids, and dextrins, and ascorbic acid.

In one example, the plasticizer includes glycerin and/or propylene glycol and/or glycerol derivatives such as propoxylated glycerol. In still another example, the plasticizer is selected from the group consisting of glycerin, ethylene glycol, polyethylene glycol, propylene glycol, glycidol, urea, sorbitol, xylitol, maltitol, sugars, ethylene bisformamide, amino acids, and mixtures thereof.

In another example, an additive may comprise a rheology modifier, such as a shear modifier and/or an extensional modifier. Non-limiting examples of rheology modifiers include but not limited to polyacrylamide, polyurethanes and polyacrylates that may be used in the fibrous elements of the present invention. Non-limiting examples of rheology modifiers are commercially available from The Dow Chemical Company (Midland, Mich.).

In yet another example, an additive may comprise one or more colors and/or dyes that are incorporated into the fibrous elements of the present invention to provide a visual signal when the fibrous elements are exposed to conditions of intended use and/or when an active agent is released from the fibrous elements and/or when the fibrous element's morphology changes.

In still yet another example, an additive may comprise one or more release agents and/or lubricants. Non-limiting examples of suitable release agents and/or lubricants include fatty acids, fatty acid salts, fatty alcohols, fatty esters, sulfonated fatty acid esters, fatty amine acetates, fatty amide, silicones, aminosilicones, fluoropolymers, and mixtures thereof. In one example, the release agents and/or lubricants may be applied to the fibrous element, in other words, after the fibrous element is formed. In one example, one or more release agents/lubricants may be applied to the fibrous element prior to collecting the fibrous elements on a collection device to form a fibrous structure. In another example, one or more release agents/lubricants may be applied to a fibrous structure formed from the fibrous elements of the present invention prior to contacting one or more fibrous structures, such as in a stack of fibrous structures. In yet another example, one or more release agents/lubricants may be applied to the fibrous element of the present invention and/or fibrous structure comprising the fibrous element prior to the fibrous element and/or fibrous structure contacting a surface, such as a surface of equipment used in a processing system so as to facilitate removal of the fibrous element and/or fibrous structure and/or to avoid layers of fibrous elements and/or plies of fibrous structures of the present invention sticking to one another, even inadvertently. In one example, the release agents/lubricants comprise particulates.

In even still yet another example, an additive may comprise one or more anti-blocking and/or detackifying agents. Non-limiting examples of suitable anti-blocking and/or detackifying agents include starches, starch derivatives, crosslinked polyvinylpyrrolidone, crosslinked cellulose, microcrystalline cellulose, silica, metallic oxides, calcium carbonate, talc, mica, and mixtures thereof.

"Conditions of intended use" as used herein means the temperature, physical, chemical, and/or mechanical conditions that a fibrous element and/or particle and/or fibrous structure of the present invention is exposed to when the fibrous element and/or particle and/or fibrous structure is used for one or more of its designed purposes. For example, if a fibrous element and/or a particle and/or a fibrous structure comprising a fibrous element is designed to be used in a washing machine for laundry care purposes, the conditions of intended use will include those temperature, chemical, physical and/or mechanical conditions present in a washing machine, including any wash water, during a laundry washing operation. In another example, if a fibrous element and/or a particle and/or a fibrous structure comprising a fibrous element is designed to be used by a human as a shampoo for hair care purposes, the conditions of intended use will include those temperature, chemical, physical and/or mechanical conditions present during the shampooing of the human's hair. Likewise, if a fibrous element and/or a particle and/or a fibrous structure comprising a fibrous element is designed to be used in a dishwashing operation, by hand or by a dishwashing machine, the conditions of intended use will include the temperature, chemical, physical and/or mechanical conditions present in a dishwashing water and/or dishwashing machine, during the dishwashing operation.

"Active agent" as used herein means an additive that produces an intended effect in an environment external to a fibrous element and/or a particle and/or a fibrous structure comprising a fibrous element of the present invention, such as when the fibrous element and/or a particle and/or fibrous structure is exposed to conditions of intended use of the fibrous element and/or a particle and/or a fibrous structure comprising a fibrous element. In one example, an active agent comprises an additive that treats a surface, such as a hard surface (i.e., kitchen countertops, bath tubs, toilets, toilet bowls, sinks, floors, walls, teeth, cars, windows, mirrors, dishes) and/or a soft surface (i.e., fabric, hair, skin, carpet, crops, plants,). In another example, an active agent comprises an additive that creates a chemical reaction (i.e., foaming, fizzing, coloring, warming, cooling, lathering, disinfecting and/or clarifying and/or chlorinating, such as in clarifying water and/or disinfecting water and/or chlorinating water). In yet another example, an active agent comprises an additive that treats an environment (i.e., deodorizes, purifies, perfumes air). In one example, the active agent is formed in situ, such as during the formation of the fibrous element and/or particle containing the active agent, for example the fibrous element and/or particle may comprise a water-soluble polymer (e.g., starch) and a surfactant (e.g., anionic surfactant), which may create a polymer complex or coacervate that functions as the active agent used to treat fabric surfaces.

"Treats" as used herein with respect to treating a surface means that the active agent provides a benefit to a surface or environment. Treats includes regulating and/or immediately improving a surface's or environment's appearance, cleanliness, smell, purity and/or feel. In one example treating in reference to treating a keratinous tissue (for example skin and/or hair) surface means regulating and/or immediately improving the keratinous tissue's cosmetic appearance and/or feel. For instance, "regulating skin, hair, or nail (keratinous tissue) condition" includes: thickening of skin, hair, or nails (e.g, building the epidermis and/or dermis and/or sub-dermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair.

In another example, treating means removing stains and/or odors from fabric articles, such as clothes, towels, linens, and/or hard surfaces, such as countertops and/or dishware including pots and pans.

"Fabric care active agent" as used herein means an active agent that when applied to a fabric provides a benefit and/or improvement to the fabric. Non-limiting examples of benefits and/or improvements to a fabric include cleaning (for example by surfactants), stain removal, stain reduction, wrinkle removal, color restoration, static control, wrinkle resistance, permanent press, wear reduction, wear resistance, pill removal, pill resistance, soil removal, soil resistance (including soil release), shape retention, shrinkage reduction, softness, fragrance, anti-bacterial, anti-viral, odor resistance, and odor removal.

"Dishwashing active agent" as used herein means an active agent that when applied to dishware, glassware, pots, pans, utensils, and/or cooking sheets provides a benefit and/or improvement to the dishware, glassware, plastic items, pots, pans and/or cooking sheets. Non-limiting examples of benefits and/or improvements to the dishware, glassware, plastic items, pots, pans, utensils, and/or cooking sheets include food and/or soil removal, cleaning (for example by surfactants) stain removal, stain reduction, grease removal, water spot removal and/or water spot prevention, glass and metal care, sanitization, shining, and polishing.

"Hard surface active agent" as used herein means an active agent when applied to floors, countertops, sinks, windows, mirrors, showers, baths, and/or toilets provides a benefit and/or improvement to the floors, countertops, sinks, windows, mirrors, showers, baths, and/or toilets. Non-limiting examples of benefits and/or improvements to the floors, countertops, sinks, windows, mirrors, showers, baths, and/or toilets include food and/or soil removal, cleaning (for example by surfactants), stain removal, stain reduction, grease removal, water spot removal and/or water spot prevention, limescale removal, disinfection, shining, polishing, and freshening.

"Weight ratio" as used herein means the ratio between two materials on their dry basis. For example, the weight ratio of filament-forming materials to active agents within a fibrous element is the ratio of the weight of filament-forming material on a dry weight basis (g or %) in the fibrous element to the weight of additive, such as active agent(s) on a dry weight basis (g or %—same units as the filament-forming material weight) in the fibrous element. In another example, the weight ratio of particles to fibrous elements within a fibrous structure is the ratio of the weight of particles on a dry weight basis (g or %) in the fibrous structure to the weight of fibrous elements on a dry weight basis (g or %—same units as the particle weight) in the fibrous structure.

"Water-soluble material" as used herein means a material that is miscible in water. In other words, a material that is capable of forming a stable (does not separate for greater than 5 minutes after forming the homogeneous solution) homogeneous solution with water at ambient conditions. "Ambient conditions" as used herein means 23° C.±1.0° C. and a relative humidity of 50%±2%.

"Weight average molecular weight" as used herein means the weight average molecular weight as determined using gel permeation chromatography according to the protocol found in Colloids and Surfaces A. Physico Chemical & Engineering Aspects, Vol. 162, 2000, pg. 107-121.

"Length" as used herein, with respect to a fibrous element, means the length along the longest axis of the fibrous element from one terminus to the other terminus. If a fibrous element has a kink, curl or curves in it, then the length is the length along the entire path of the fibrous element from one terminus to the other terminus.

"Diameter" as used herein, with respect to a fibrous element, is measured according to the Diameter Test Method described herein. In one example, a fibrous element of the present invention exhibits a diameter of less than 100 µm and/or less than 75 µm and/or less than 50 µm and/or less than 25 µm and/or less than 20 µm and/or less than 15 µm and/or less than 10 µm and/or less than 6 µm and/or greater than 1 µm and/or greater than 3 µm.

"Triggering condition" as used herein in one example means anything, as an act or event, that serves as a stimulus and initiates or precipitates a change in the fibrous element and/or particle and/or fibrous structure of the present invention, such as a loss or altering of the fibrous element's and/or fibrous structure's physical structure and/or a release of an additive, such as an active agent therefrom. In another example, the triggering condition may be present in an environment, such as water, when a fibrous element and/or particle and/or fibrous structure of the present invention is added to the water. In other words, nothing changes in the water except for the fact that the fibrous element and/or fibrous structure of the present invention is added to the water.

"Morphology changes" as used herein with respect to a fibrous element's and/or particle's morphology changing means that the fibrous element experiences a change in its physical structure. Non-limiting examples of morphology changes for a fibrous element and/or particle of the present invention include dissolution, melting, swelling, shrinking, breaking into pieces, exploding, lengthening, shortening, and combinations thereof. The fibrous elements and/or particles of the present invention may completely or substantially lose their fibrous element or particle physical structure or they may have their morphology changed or they may retain or substantially retain their fibrous element or particle physical structure as they are exposed to conditions of intended use.

"By weight on a dry fibrous element basis" and/or "by weight on a dry particle basis" and/or "by weight on a dry fibrous structure basis" means the weight of the fibrous element and/or particle and/or fibrous structure, respectively, measured immediately after the fibrous element and/or particle and/or fibrous structure, respectively, has been conditioned in a conditioned room at a temperature of 23° C.±1.0° C. and a relative humidity of 50%±10% for 2 hours. In one example, by weight on a dry fibrous element basis and/or dry particle basis and/or dry fibrous structure basis means that the fibrous element and/or particle and/or fibrous structure comprises less than 20% and/or less than 15% and/or less than 10% and/or less than 7% and/or less than 5% and/or less than 3% and/or to 0% and/or to greater than 0% based on the dry weight of the fibrous element and/or particle and/or fibrous structure of moisture, such as water, for example free water, as measured according to the Water Content Test Method described herein.

"Total level" as used herein, for example with respect to the total level of one or more active agents present in the fibrous element and/or particle and/or fibrous structure, means the sum of the weights or weight percent of all of the subject materials, for example active agents. In other words, a fibrous element and/or particle and/or fibrous structure may comprise 25% by weight on a dry fibrous element basis and/or dry particle basis and/or dry fibrous structure basis of an anionic surfactant, 15% by weight on a dry fibrous element basis and/or dry particle basis and/or dry fibrous structure basis of a nonionic surfactant, 10% by weight of a chelant on a dry fibrous element basis and/or dry particle basis and/or dry fibrous structure basis, and 5% by weight of a perfume a dry fibrous element basis and/or dry particle basis and/or dry fibrous structure basis so that the total level of active agents present in the fibrous element and/or particle and/or fibrous structure is greater than 50%; namely 55% by weight on a dry fibrous element basis and/or dry particle basis and/or dry fibrous structure basis.

"Fibrous structure product" as used herein means a solid form, for example a rectangular solid, sometimes referred to as a sheet, in this case one or more fibrous structures of the present invention, that comprises a plurality of fibrous elements and a plurality of particles. The fibrous structure products comprise one or more active agents, for example an effervescent agent, a fabric care active agent, a dishwashing active agent, a hard surface active agent, and mixtures thereof, present in the fibrous elements and/or particles of the fibrous structure and/or fibrous structure product. In one example, a fibrous structure product of the present invention comprises one or more surfactants, one or more enzymes (such as in the form of an enzyme prill), one or more perfumes and/or one or more suds suppressors. In another example, a fibrous structure product of the present invention comprises a builder and/or a chelating agent. In another example, a fibrous structure product of the present invention comprises a bleaching agent (such as an encapsulated bleaching agent). In one example, the fibrous structure product is a toilet bowl cleaning product.

"Different from" or "different" as used herein means, with respect to a material, such as a fibrous element as a whole and/or a filament-forming material within a fibrous element and/or an active agent within a fibrous element, that one material, such as a fibrous element and/or a filament-forming material and/or an active agent, is chemically, physically and/or structurally different from another material, such as a fibrous element and/or a filament-forming material and/or an active agent. For example, a filament-forming material in the form of a filament is different from the same filament-forming material in the form of a fiber. Likewise, a starch polymer is different from a cellulose polymer. However, different molecular weights of the same material, such as different molecular weights of a starch, are not different materials from one another for purposes of the present invention.

"Random mixture of polymers" as used herein means that two or more different filament-forming materials are randomly combined to form a fibrous element. Accordingly, two or more different filament-forming materials that are orderly combined to form a fibrous element, such as a core and sheath bicomponent fibrous element, is not a random mixture of different filament-forming materials for purposes of the present invention.

"Associate," "Associated," "Association," and/or "Associating" as used herein with respect to fibrous elements and/or particle means combining, either in direct contact or in indirect contact, fibrous elements and/or particles such that a fibrous structure is formed. In one example, the associated fibrous elements and/or particles may be bonded together for example by adhesives and/or thermal bonds. In another example, the fibrous elements and/or particles may be associated with one another by being deposited onto the same fibrous structure making belt and/or patterned belt.

"Aperture" as used herein means an opening or void or indentation in a fibrous structure which is distinct from the surrounding fibrous structure. In one example, an aperture may comprise any feature where there is a localized disruption of the fibrous structure. In one example, an aperture may comprise a local indentation or localized disruption of the basis weight, thickness, or caliper of the fibrous structure. In another example, an aperture may be an opening in a fibrous structure wherein the opening passes substantially or completely through both generally planar surfaces of the fibrous structure, through one generally planar surface of the fibrous structure, or even through neither planar surface of the fibrous structure. In another example, an aperture may be an opening in the fibrous structure wherein there is a complete opening, partial opening, or even no apparent opening. In still another example, an aperture may comprise a feature which is an embossment in the fibrous structure. In even another example, an aperture is an internal feature to a fibrous structure and/or multi-ply fibrous structure wherein for example the aperture feature may be present on an internal ply of a multi-ply fibrous structure. In even yet another example, an aperture comprises an opening or void or indentation in a fibrous structure wherein the opening or void or indentation is a non-random and/or designed and/or fabricated opening, void, or indentation rather than a random pore that exists between and/or amongst fibrous elements of a fibrous structure resulting from the collection and inter-entangling of fibrous elements on a collection device.

"Machine Direction" or "MD" as used herein means the direction parallel to the flow of the fibrous structure through the fibrous structure making machine and/or fibrous structure product manufacturing equipment.

"Cross Machine Direction" or "CD" as used herein means the direction perpendicular to the machine direction in the same plane of the fibrous structure and/or fibrous structure product comprising the fibrous structure.

"Ply" or "Plies" as used herein means an individual fibrous structure optionally to be disposed in a substantially contiguous, face-to-face relationship with other plies, forming a multiple ply fibrous structure. It is also contemplated that a single fibrous structure can effectively form two "plies" or multiple "plies", for example, by being folded on itself.

As used herein, the articles "a" and "an" when used herein, for example, "an anionic surfactant" or "a fiber" is understood to mean one or more of the material that is claimed or described.

All percentages and ratios are calculated by weight unless otherwise indicated. All percentages and ratios are calculated based on the total composition unless otherwise indicated.

Unless otherwise noted, all component or composition levels are in reference to the active level of that component or composition, and are exclusive of impurities, for example, residual solvents or by-products, which may be present in commercially available sources.

Matrix Particles

As shown in FIG. 1, an example of a matrix particle 10 of the present invention comprises one or more matrix materials 12 in the form of a porous structure comprising a plurality of pores 13, and one or more hydrophobic active agents 14 present within at least one of the pores. As seen in FIG. 1, this example of a matrix particle 10 is a hollow matrix particle. In another example, the matrix particle may be non-hollow, for example a continuous porous structure (formed by the one or more matrix materials) comprising a plurality of pores wherein at least one hydrophobic active agent is present in at least one of the pores.

In one example, the matrix particles of the present invention are water-soluble. In another example, the matrix particles of the present invention are water-insoluble. In one example a plurality of matrix particles may comprise water-soluble matrix particles and water-insoluble matrix particles.

In one example, the one or more matrix materials are selected for the matrix particle based upon their compatibility with the one or more hydrophobic active agents, especially the emulsion comprising the one or more hydrophobic active agents into which the one or more matrix materials are added during the process of making the matrix particle.

In one example, when the matrix particle is a water-soluble matrix particle, for example comprises one or more of the hydrophobic active agents, for example a perfume and/or a silicone, the one or more hydrophobic active agents releases from the matrix particle upon the matrix particle contacting a polar solvent, for example water, and/or upon dissolution of a portion or the entire matrix particle and/or one or more, for example all of the matrix materials.

In one example, when the matrix particle is a water-insoluble matrix particle, for example comprises one or more hydrophobic active agents, for example a perfume and/or a silicone, the one or more hydrophobic active agents releases from the matrix particle upon the matrix particle contacting a polar solvent, which swells the matrix particle and facilitates diffusion, for example increases diffusion of the one or more hydrophobic active agents out of the water-insoluble matrix particle. The diffusion of the one or more hydrophobic active agents may not be complete or fast. This ability to diffuse from the matrix particle is aided by the fact that the one or more matrix materials of the matrix particle are not crosslinked with a crosslinking agent, especially in the case of the hydrophobic active agents comprising silicone.

Leakage, in this case diffusion, of the one or more hydrophobic active agents whether the matrix particle is water-soluble or water-insoluble is impacted by the viscosity of the hydrophobic active agents. For example, the silicone hydrophobic benefits agents exhibit a higher viscosity than the perfume hydrophobic active agents and therefore the silicones leak/diffuse from the matrix particles less rapidly and/or less completely than the perfumes, especially when the matrix particles are in a dry state. In light of this fact, in one example a matrix particle comprising one or more silicones as the hydrophobic active agents, for example void or substantially void of perfumes, comprises uncrosslinked matrix materials. And in another example, a matrix particle comprising one or more perfumes as the hydrophobic active agents, for example void or substantially void of silicones, comprises crosslinked matrix materials.

The design of the matrix particles can result in more robust particles, even if there is some fracture of the matrix particles. In the case of a fracture of the matrix particle, only that fractured portion of the matrix particle releases its hydrophobic active agent, such as a perfume, the remaining portions of the fractured matrix particle retains its hydrophobic active agents until exposed to conditions that trigger release and/or are fractured again. This ability of the matrix particles to fracture but have portions of the matrix particle retain its hydrophobic active agents is advantageous over encapsulated particles, such as core/shell encapsulates wherein fracture of the core/shell encapsulates results in the total loss of the benefit agents within the core/shell encapsulates.

In one example, the matrix particles, for example matrix particles comprising starch matrix materials and perfume hydrophobic active agents, may exhibit a leakage of less than or equal to 20%, alternatively less than or equal to 18%, alternatively less than or equal to 16%, alternatively less than or equal to 15%, alternatively less than or equal to 13%, alternatively less than or equal to 10%, alternatively less than or equal to 8%, alternatively less than or equal to 6%, alternatively less than or equal to 5%, alternatively less than or equal to 4%, alternatively less than or equal to 3%, alternatively less than or equal to 2%, and/or alternatively less than or equal to 1%, according to the Analysis of Free Perfume in Perfume Matrix Particles described herein.

In one example, the matrix particle may comprise from about 10-70 wt. % of one or more hydrophobic active agents, from about 21-72 wt. % of one or more matrix materials, from about 3-12 wt. % of a crosslinking agent, and from about 1-6 wt. % of a catalyst, by total weight of the matrix particle (not to exceed 100%).

The crosslinking agent, when present, can be present in an amount effective (in the presence of a catalyst) to crosslink the matrix material, for example polysaccharide, such as starch, to an extent effective to provide the matrix particles with desired durability. The amount can be for example at least about 1 wt. % and/or at least about 2 wt. % and/or at least about 3 wt. % and/or at least about 3.80 wt. % and/or at least about 5 wt. % and/or to about 15 wt. % and/or to about 12 wt. % and/or to about 10 wt. % and/or to about 8 wt. % by total weight of the matrix particle.

Non-limiting examples of suitable crosslinking agents may be selected from the group consisting of dimethyldihydroxy urea, dimethyloldihhyrodyethylene urea, dimethylol urea, dihydroxyethylene urea, dimethylolethylene urea, dimethyldihydroxyethylene urea, citric acid, tartaric acid, malic acid, succinic acid, glutaric acid, citraconic acid, itaconic acid, tartrate monosuccinic acid, maleic acid, poly (acrylic acid), poly(methacrylic acid), poly(maleic acid), poly(methylvinylether-co-maleate) copolymer, copolymers of acrylic acid and copolymers of maleic acid, and mixtures thereof.

In addition to the crosslinking agent, the matrix material may further comprise a catalyst in an amount effective to catalyze the crosslinking of the matrix material, for example polysaccharide, such as starch, to an extent effective to provide the matrix particles with desired durability. The amount can be for example at least about 0.1 wt. % and/or at least about 0.5 wt. % and/or at least about 1 wt. % and/or at least about 2 wt. % and/or to about 7 wt. % and/or to about 6 wt. % and/or to about 5 wt. % and/or to about 2.5 wt. % by total weight of the matrix particle.

The catalyst, when present, may be a reducing agent and/or electron donor and may be selected from the group consisting of ammonium chloride, ammonium sulfate, aluminum chloride, magnesium chloride, magnesium nitrate, sodium hypophosphite, and mixtures thereof.

Flow aids, for example silica flow aids may be included in the matrix particles. The silica flow aid may include precipitated silica, fumed silica, hydrophobic silica, and mixtures thereof. However, adding a flow aid, for example a silica flow aid, may prevent and/or inhibit agglomeration of the matrix particles. Therefore, in one example, the matrix particles of the present invention may be free of and/or substantially free of a flow aid, for example a silica flow aid. In another example the matrix particles may comprise less than 1 wt. % and/or less than 0.5 wt. % and/or less than 0.1 wt. % and/or less than 0.05 wt. % flow aid, for example a silica flow aid, by total weight of the matrix particle.

In one example, a matrix particle comprises one or more matrix materials in the form of a porous structure comprising a plurality of pores, wherein one or more hydrophobic active agents are present in at least one of the pores and/or are dispersed throughout the one or more matrix materials, and optionally, wherein at least one of the one or more hydrophobic active agents is released from the matrix particle upon the matrix particle contacting water and/or upon dissolution of a portion or the entire matrix particle and/or one or more, for example all of the matrix materials.

In one example, a matrix particle of the present invention comprises one or more matrix materials, for example uncrosslinked polyvinyl alcohol, and one or more hydrophobic active agents, for example silicone, such as an aminosilicone, for example terminal aminosilicone. In one example, such a matrix particle may be agglomerated with other matrix particles, same or different, for example the same, to form an agglomerated particle comprising a plurality of the matrix particles.

In one example, a matrix particle of the present invention comprises one or more matrix materials, for example uncrosslinked polyvinyl alcohol, and one or more hydrophobic active agents, for example perfume. In one example, such a matrix particle may be agglomerated with other matrix particles, same or different, for example the same, to form an agglomerated particle comprising a plurality of the matrix particles.

In one example, at least one of the one or more matrix materials is a water-soluble matrix material. In one example, at least one of the one or more matrix materials is selected from the group consisting of: polyvinyl alcohol, polysaccharides, gums, gelatin, dextrins, polyethylene glycols, gum arabic, larch, pectin, tragacanth, locust bean, guar, alginates, carrageenans, cellulose gums, karaya, and mixtures thereof.

In one example, the matrix particle exhibits a size of less than 500 µm and/or less than 400 um and/or less than 300 µm and/or less than 200 µm and/or less than 100 µm and/or to about 20 um and/or to about 30 µm and/or from about 20 µm to about 500 µm and/or from about 20 µm to about 400 µm and/or from about 20 µm to about 300 µm and/or from about 20 µm to about 200 µm and/or from about 20 µm to about 100 µm and/or from about 20 to about 90 µm and/or from about 30 µm to about 80 µm as measured according to the Median Particle Size Test Method described herein.

a. Matrix Materials

The matrix particle of the present invention may comprise from about 10 wt. % to about 90 wt. % and/or from about 30 wt. % to about 85 wt. % and/or from about 40 wt. % to about 85 wt. % and/or from about 45 wt. % to about 80 wt. % and/or from about 50 wt. % to about 75 wt. % of one or more matrix materials by total weight of the matrix particle.

Non-limiting examples of suitable matrix materials include matrix materials selected from the group consisting of water-soluble polymers, polyvinyl alcohol, polysaccharides, crosslinking agents, catalysts, polyethylene glycols (PEG), starches, gums, gelatin, dextrins, as well as hydrolyzed gums and hydrolyzed gelatin, polyacrylic acid and its copolymers, polyvinylpyrrolidone and its copolymers, polyacrylamide and its copolymers, polyvinylmethyl ether, polyethyleneimine, polymethacrylic acid, N-isopropyl acrylamide, n-n-dimethylacrylamide, other water-soluble acrylic-based polymers, polyvinyloxazolidone, polycaprolactam, polystyrene sulfonate, polyvinyl formamide, polyvinyl amine, and mixtures thereof. Non-limiting examples of suitable starches include gum arabic, larch, pectin, tragacanth, locust bean, guar, alginates such as sodium alginate and propylene glycol alginates, carrageenans, cellulose gums such as carboxymethyl cellulose, and karaya. Some of the suitable matrix materials have melting points and thus can be melted, but for the present invention, in one example, the suitable matrix materials are soluble in a polar solvent, for example water, which results in the matrix materials forming a porous structure comprising a plurality of pores upon removal of the polar solvent, for example water, during the drying process, for example spray drying process. Such a porous structure formed by the matrix materials is not formed upon cooling a melted matrix material. In other words, cooling of a melted matrix material forms a nonporous structure.

In one example, at least one of the one or more matrix materials is selected from the group consisting of: polyvinyl alcohol, polysaccharides, gums, gelatin, dextrins, polyethylene glycols, gum arabic, larch, pectin, tragacanth, locust bean, guar, alginates, carrageenans, cellulose gums, karaya, polyacrylic acid, polyvinylpyrrolidone, polyacrylamide, and mixtures thereof.

In one example, at least one of the one or more matrix materials comprises polyvinyl alcohol, for example water-soluble polyvinyl alcohol.

In one example, at least one of the one or more matrix materials comprises a polysaccharide, for example starch.

In one example, at least one of the one or more matrix materials comprises polyethylene glycol in its dissolved form, for example an aqueous solution of polyethylene glycol. Polyethylene glycol in its melted and subsequently cooled form is not within the scope of the present invention.

In another example, a matrix material may include dextrins, for example carboxylated dextrins derived from oxidized starches containing a controlled amount of carboxyl groups. These carboxylated dextrins may be prepared from oxidized cereal starches such as corn, wheat, waxy maize and waxy sorghum starches. Carboxylated dextrins derived from oxidized root starches, such as tapioca and potato starches, may also be used. All of these carboxylated dextrins may be compatible with volatile oils, like perfumes.

The matrix material may comprise polyethylene glycol (PEG). The PEG can have a molecular weight from about 4000 to about 10,000 g/mol and/or from about 6000 to about 9,000 g/mol and/or from about 7000 to about 8000 g/mol. In one example, the PEG may have a molecular weight from about 4000 to about 8000 g/mol. The PEG can be solid at room temperature (about 23° C.) with a melting point of about 60° C. In one example, the matrix particle may comprise PEG 8000.

The matrix material may comprise a polysaccharide, which can be present in an amount effective to provide the desired structural and release properties for the matrix particle, for instance at a level of from at least about 5 wt. % and/or at least about 10 wt. % and/or at least about 21 wt. % and/or at least about 25 wt. % to about 80 wt. % and/or to about 72 wt. % and/or to about 60 wt. % and/or to about 50 wt. % by total weight of the matrix particle. The polysaccharide can be selected from the group consisting of octenyl succinic acid anhydride modified starch including modified corn starch, gum arabic, xanthan gum, gellan gum, pectin gum, konjac gum and carboxyalkyl cellulose, and mixtures thereof.

b. Hydrophobic Active Agents

The matrix particle of the present invention may comprise from about 10 wt. % to about 90 wt. % and/or from about 15 wt % to about 70 wt % and/or from about 20 wt % to about 50 wt % and/or from about 30 wt % to about 45 wt % of one or more hydrophobic active agents by total weight of the matrix particle.

The hydrophobic active agent may be a nonpolar material. The hydrophobic active agent may be selected from the group consisting of: perfumes, essential oils, oils, vitamin oils, vegetable oils, silicones, shea butter, cocoa butter, petrolatum, tea tree oil, medium-chain ($C_6$-$C_{12}$) triglycerides, and mixtures thereof. In one example, the hydrophobic active agent may be a perfume. In another example, the hydrophobic active agent may include a perfume in combination with a silicone, such as a terminal aminosilicone and/or polydimethylsilicone, and/or oligomeric vegetable oils. In another example, the hydrophobic active agent can include two or more and/or three or more different perfumes.

In one example, at least one of the one or more hydrophobic active agents is selected from the group consisting of: perfumes, essential oils, oils, vitamin oils vegetable oils, silicones, shea butter, cocoa butter, petrolatum, grapeseed oil, sunflower oil, olive oil, argan oil, Vitamin E, and mixtures thereof.

In one example, the hydrophobic active agent may comprise a water-insoluble hydrophobic active agent particle, such as silica, titanium dioxide, and/or sodium hexametaphosphate (commonly referred to as Glass H®), and mixtures thereof.

When the hydrophobic active agent comprises a perfume, the perfume may include perfume compositions comprising perfume materials having a LogP (logarithm of octanol-water partition coefficient) of from about 2 to about 12 and/or from about 2.5 to about 8 and/or from about 2.5 to about 6. In one example, the perfume may exhibit a boiling point of less than about 280° C. and/or from about 50° C. to less than about 280° C. and/or from about 50° C. to less than about 265° C. and/or from about 80° C. to less than about 250° C. In one example, the perfume may exhibit an ODT (odor detection threshold) of less than about 100 parts per billion (ppb) and/or from about 0.00001 ppb to less than about 100 ppb and/or from about 0.00001 ppb to less than about 50 ppb and/or from about 0.00001 ppb to less than about 20 ppb.

A wide variety of natural and synthetic chemical ingredients useful as perfumes and/or perfumery ingredients including but not limited to aldehydes, ketones, esters, and mixtures thereof may be used as a hydrophobic active agent, for example as a perfume in the matrix particles of the present invention. Non-limiting examples of essential oils, which can be used as one or more of the hydrophobic active agents, include those obtained from orange oil, lemon oil, thyme, lemongrass, citrus, anise, clove, aniseed, rose extract, lavender, citronella, eucalyptus, peppermint, camphor, sandalwood, cinnamon leaf, cedar, pine oil, musk, patchouli, balsamic essence, and mixtures thereof. Essential oils that exhibit antimicrobial properties may also be used as one or more hydrophobic active agents.

Other hydrophobic active agents that may be used include vitamin oils. Non-limiting examples of vitamin oils include fat-soluble vitamin-active materials, pro vitamins, and pure or substantially pure vitamins, both natural and synthetic, or chemical derivatives thereof, crude extractions containing such substances, vitamin A, vitamin D, and vitamin E active materials as well as vitamin K, carotene and the like, or mixtures of such vitamin materials.

Non-limiting examples of vegetable oils, which may be used has hydrophobic active agents, include but are not limited to oils derived from palm, corn, canola, sunflower, safflower, rapeseed, castor, olive, soybean, coconut and the like, in both the unsaturated forms and hydrogenated forms, and mixtures thereof.

In one example, a diluent may be mixed with the hydrophobic active agent. The diluent suitable to be mixed with the hydrophobic active agents may be miscible in the hydrophobic active agent, for example in a perfume oil or other oil or silicone and may act to reduce the volatility of the hydrophobic active agent, for example a fragrance oil. Non-limiting examples of diluents may include isopropyl myristate, iso E super, triethyl citrate, vegetable oils, hydrogenated oils, and mixtures thereof.

In one example, the hydrophobic active agents exhibit a particle and/or droplet size of at least 0.02 μm to about 200 μm and/or at least 0.1 μm to about 100 μm and/or from about 0.25 μm to about 100 μm and/or from about 0.5 μm to about 75 μm and/or from about 1 μm to about 50 μm and/or from about 1 μm to about 30 μm and/or from about 2 μm to about 15 μm and/or from about 5 μm to about 10 μm. In one example, the droplet size of the hydrophobic active agents is greater than 5 μm and/or greater than 10 μm and/or greater than 15 μm and/or greater than 20 μm and/or greater than 25 μm and/or less than 100 μm and/or less than 75 μm and/or less than 50 μm and/or less than 40 μm. The droplet size of the hydrophobic active agents can be measured by any suitable method know in the art. For example, the droplet size of the hydrophobic active agents may be measured prior to making the matrix particle for example when the hydrophobic active agent is present as droplets in an emulsion and/or the droplet size of the hydrophobic active agents may be measured by dissolving in water the matrix material of the matrix particle leaving the hydrophobic active agent droplets within the water.

Process for Making Matrix Particles

Figure 2:
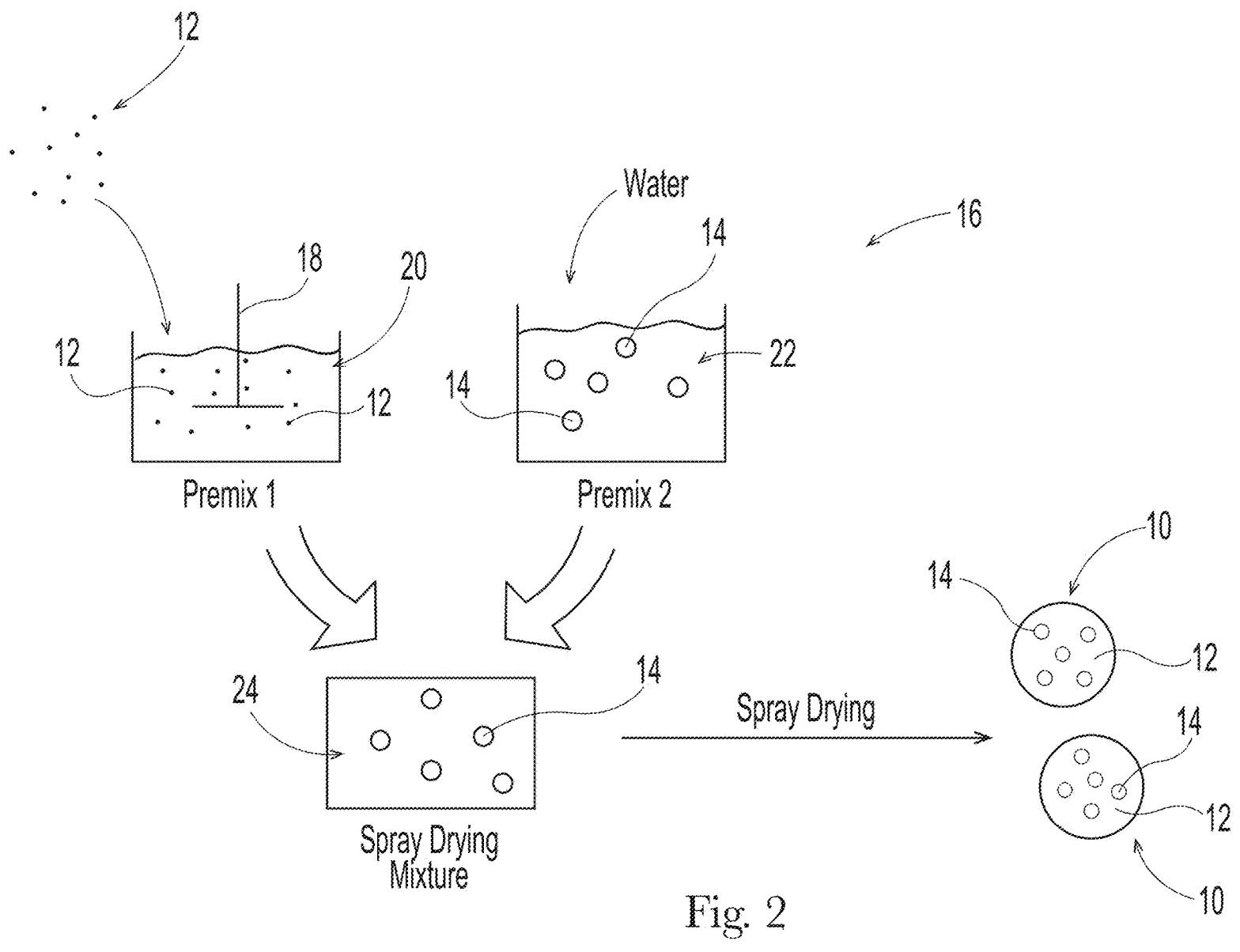

In one example, as shown in FIG. 2, the matrix particles 10 of the invention may be made by a process 16 comprising the steps of:
a. dissolving one or more matrix materials 12 in a polar solvent, for example water, such as distilled water, with stirring, for example by an overhead stirrer 18, and heating the one or more matrix materials 12 in the water, for example to about 90° C., to help facilitate dissolution of the one or more matrix materials 12 to form a solution 20 (an aqueous solution of the matrix materials), for example Premix 1;
b. providing an emulsion, for example an aqueous emulsion, comprising one or more hydrophobic active agents 14, for example a commercially available emulsion such as Silsoft 253, a pre-made terminal aminosilicone emulsion commercially available from Momentive, which contains amodimethicone, emuisfiers ($C_{11-15}$ pareth 7, laureth 9, glycerin and trideceth 12) and water with a silicone content of 20%, or making an emulsion 22 by adding one or more hydrophobic active agents 14 in water, for example distilled water, with or without an emulsifying agent, to form the emulsion 22, for example Premix 2;
c. mixing the solution from Step a with the emulsion from Step b to form a spray drying mixture 24 comprising the solution from Step a and the emulsion comprising hydrophobic active agents 14 from Step b; and
d. spray drying the spray drying mixture 24 to form matrix particles 10 comprising one or more matrix materials 12 and one or more hydrophobic active agents 14.

In another example, the matrix particles 10 of the invention may be made by a process comprising the steps of:
a. mixing one or more hydrophobic active agents with one or more matrix materials in the presence of water to provide an emulsion, for example an aqueous emulsion;
b. agitating the emulsion to provide a modified emulsion containing hydrophobic active agent droplets, for example hydrophobic active agent droplets with a volume average diameter of less than 200 μm and/or less than 100 μm and/or less than 75 μm and/or less than 50 μm and/or less than 40 μm and/or greater than 0.02 μm and/or greater than 0.25 μm and/or greater than 5 μm; and
c. producing matrix particles comprising the one or more matrix materials and the one or more hydrophobic active agents dispersed throughout the matrix materials from the modified emulsion.

The step of producing matrix particles may comprise one or more of the following optional steps:
d. optionally adding to the modified emulsion a cross-linking agent and/or catalyst to provide a spray-ready emulsion;
e. optionally spray drying the spray-ready emulsion to provide a modified powder, which when dried forms the matrix particles; and
f. optionally heating the modified powder to form the matrix particles.

Optionally, a desiccant can be added to the modified powder to absorb any moisture that may be released from the matrix particle during heating, such that the moisture does not act to plasticize the matrix particle and form large aggregates (greater than 2000 μm). Suitable desiccants include but are not limited to calcium sulfate, sodium sulfate, calcium silicate, hydrophilic aluminosilicates, magnesium sulfate, silica gel, crosslinked polyacrylates, and the like. It can be desirable to have the desiccant particle size at least 5 times the median particle size of the modified powder being heated, such that after the modified powder heating process, the desiccants can be removed via sieving. The amount of dessicant, when present, can be for example at least about 0.05 wt. % and/or at least about 0.10 wt. % and/or at least about 0.5 wt. % and/or at least about 1 wt. % and/or to about 10 wt. % and/or to about 7 wt. % and/or to about 5 wt. % and/or to about 2.5 wt. % by total weight of the matrix particle.

In another example of the present invention, which is shown in FIG. 2 with the exception of Premix 2, which in this example is replaced with neat hydrophobic active agent particles, for example water-insoluble hydrophobic active agent particles such as silica, wherein the matrix particles 10 are made by a process 16 comprising the steps of:
a. dissolving one or more matrix materials 12 in a polar solvent, for example water, such as distilled water, with stirring, for example by an overhead stirrer 18, and heating the one or more matrix materials 12 in the water, for example to about 90° C., to help facilitate dissolution of the one or more matrix materials 12 to form a solution 20, for example Premix 1;
b. adding one or more hydrophobic active agents, for example one or more hydrophobic active agent particles, 14, such as silica;
c. mixing the solution from Step a with the hydrophobic active agents from Step b to form a spray drying mixture 24 comprising the solution from Step a and the hydrophobic active agents 14 from Step b; and
d. spray drying the spray drying mixture 24 to form matrix particles 10 comprising one or more matrix materials 12 and one or more hydrophobic active agents 14, for example one or more hydrophobic active agent particles.

In one example, the matrix particles of the present invention are made using the methods and/or equipment described in U.S. Pat. Nos. 8,939,388, 9,332,776, 9,551,527, 9,861,945, and/or 9,993,787 all of which are incorporated herein by reference.

Agglomerated Particles

The matrix particles of the present invention may be agglomerated to form agglomerated particles, for example agglomerated particles suitable for use in fibrous structures. Agglomeration of the matrix particles can be beneficial because when the matrix particles are too small, they fall through a fibrous structure and are not retained by the fibrous structure and/or are easily knocked off the outer surfaces of the fibrous structure. However, if the agglomerated particles are too large, they are noticeable, and the consumer complains that the dissolvable structure feels gritty during use.

Agglomeration also aids in maintaining consistent formulation of the finished product when multiple smaller matrix particles are used in one finished fibrous structure. Segregation of particle mixtures is an extremely common problem in solids processing. Agglomerating multiple matrix particles at the correct ratio for the finished product ensures delivery of all actives at the desired level.

The agglomerated particles may exhibit a size of from about 100 μm to about 1500 μm, and/or from 150 μm to about 1250 μm and/or from about 200 μm to about 1000 μm, and/or from about 300 μm to about 800 μm as measured according to the Median Particle Size Test Method described herein. In one example, the agglomerated particles exhibit a size of from about 200 μm to about 500 μm as measured according to the Median Particle Size Test Method described herein.

In one example, the agglomerated particle exhibits a size of greater than 200 μm and/or greater than 200 μm to about 1600 μm and/or greater than 200 μm to about 1000 μm and/or from about 300 μm to about 800 μm and/or from about 300 μm to about 500 μm as measured according to the Median Particle Size Test Method described herein.

Agglomerated particle size is controlled by the initial matrix particle size, binder selection, and the time of mixing after binder addition in the agglomeration process. In one example, a matrix particle, for example exhibiting a size of from about 400 μm to about 500 μm as measured according to the Median Particle Size Test Method described herein, is chosen as a "seed particle", the binder, for example a nonionic binder, used to stick to smaller matrix particles, for example matrix particles having a size of from about 50 μm to about 100 μm as measured according to the Median Particle Size Test Method described herein.

In one example, the agglomerated particles are preformed before incorporating them into a fibrous structure. In one example, a binder may be used to aid in, assist in, and/or facilitate in agglomerating matrix particles together and/or keep the agglomerated particles together. A binder may be any material or substance that holds or draws other materials together to form a cohesive whole mechanically, chemically, or as an adhesive. The binder choice can have an effect on the forming of the agglomerated particle. Binders may include those that are nonionic to minimize the interaction with the reactants within the matrix particle, however, polymeric and ionic binders can also be used. Suitable binders include, but are not limited to, nonionic surfactants, nonionic polymers, ethoxylated alcohols, sorbitan derivatives, polyethylene glycols, corn syrup, paraffin, waxes, fatty alcohols, and mixtures thereof. In one example, the binder, when present, may be selected from the group consisting of: polyvinylpyrrolidone (PVP) and copolymers thereof, polyacrylic acid and copolymers thereof, maltodextrin, polysaccharides, for example starch and starch derivatives, and mixtures thereof. Binders, when present, may be included in the agglomerated particle at a level of from about 0.05 weight % to about 10 weight % and/or from about 1 weight % to about 5 weight % of the agglomerated particle.

Optionally, a humectant may be added to the agglomerated particle. Suitable humectants may include salts, sugars, acids, glycols, inorganics and combinations thereof. Suitable humectants can be selected from PEG400, PEG 600, sorbitol, potassium carbonate, sodium chloride, Potassium acetate, PEG 4000, zeolite, corn syrup, glycerol, fructose, sucrose, citric acid, tartaric acid, malic acid, lactic acid, magnesium chloride, and mixtures thereof. When present, the humectant may be present at a level of from about 0.1 to about 15 wt. % and/or from about 1 to about 7 weight % of the agglomerated particle.

Optionally, flow aids may be added to the agglomerated particles, for example at low levels (for example less than about 1 wt. % and/or less than about 0.5 wt. % and/or less than 0.1 wt. % and/or less than about 0.05 wt. % of the agglomerated particle to help make the agglomerated particle flow better. Non-limiting examples of suitable flow aids for the agglomerated particles include Zeolite A, precipitated silica, precipitated silicates, fly ash, talc, starch, clays, metallic stearates, phosphates, amides, polysaccharides, sugars, and mixtures thereof. Particularly suitable materials include Zeolite A, silica, sugars and mixtures thereof.

In one example, matrix particles comprising a perfume ("perfume matrix particles) may be agglomerated with other perfume matrix particles where the perfumes are the same or different. The perfume matrix particles may also be agglomerated with different matrix particles, such as matrix particles comprising effervescent agents, silicones, surfactants, cationic polymers, antimicrobials including antibacterials and antifungals, and/or mixtures thereof.

In one example, matrix particles comprising a silicone ("silicone matrix particles) may be agglomerated with other silicone matrix particles where the silicones are the same or different. The silicone matrix particles may also be agglomerated with different matrix particles, such as matrix particles comprising effervescent agents, perfumes, surfactants, cationic polymers, antimicrobials including antibacterials and antifungals, and/or mixtures thereof.

Non-limiting examples of agglomerated particles are disclosed in WO2018/140675 hereby incorporated by reference herein.

In one example, the agglomerated particles exhibit an agglomerate bulk density of less than 700 g/L and/or less than 600 g/L and/or less than 500 g/L and/or less than 400 g/L and/or greater than 25 g/L and/or greater than 50 g/L as measured using the re-pour density measurement method. In this method, the agglomerated particles are dropped 12 inches from a funnel into a cup of known volume. The pile of agglomerated particles above the cup rim is then scrapped away, leaving a completely full cup of agglomerated particles. The mass of the remaining agglomerated particles in the full cup is measured gravimetrically. The bulk density is then found by dividing the mass of the remaining agglomerated particles by the volume of the cup, in this case reported in g/L.

Process for Making Agglomerated Particles

Figure 3:
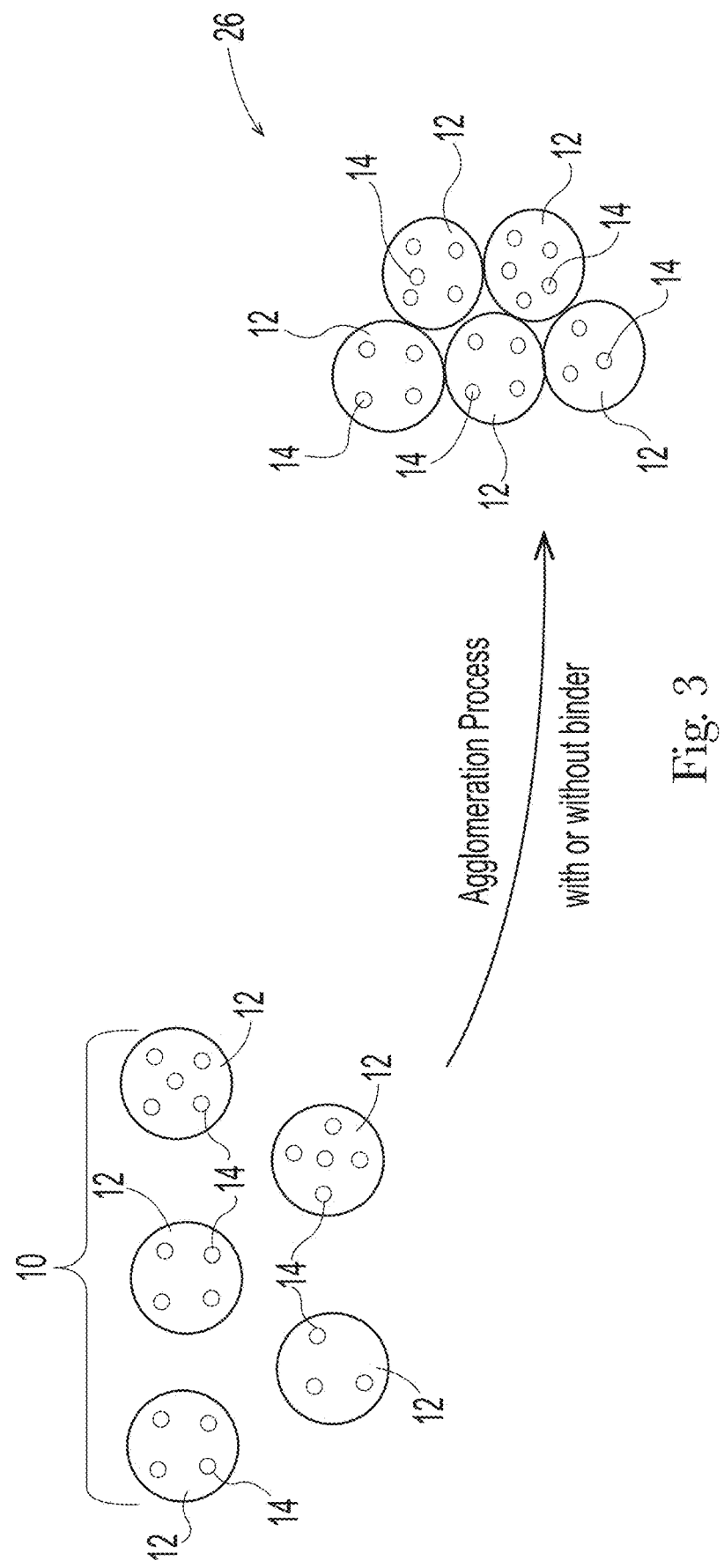
FIG. 3 is a schematic representation of an example of a process for making an agglomerated particle according to the present invention.

In one example, as shown in FIG. 3, the agglomerated particles 26 may be made by a process comprising mixing a plurality of matrix particles 10 comprising one or more matrix materials 12 and one or more hydrophobic active agents 14 together, with or without a binder, in one example with a binder, such that the agglomerated particles 26 are formed.

The agglomerated particles may be made by mixing a plurality of matrix particles together in a convective or tumbling solids mixer, for example that includes paddle mixers and/or v-blenders for at least 5 minutes, with or without a binder and/or humectant. Binder can be added and mixed for an additional 5 min, or longer for larger agglomerated particles or shorter for smaller agglomerated particles. Optionally, a flow aid may be added after the agglomerated particles have reached target size. Mixing continues for approximately another minute. The agglomerated particles may be transferred into a storage vessel until ready for use.

Agglomerated particle size may be controlled by the initial raw material particle size, binder selection, and the time of mixing after binder addition in the agglomeration process.

Fibrous Structure

The fibrous structure of the present invention comprises a plurality of fibrous elements, for example a plurality of filaments, and one or more particles, for example one or more matrix particles and/or agglomerated particles according to the present invention.

In one example, the fibrous elements and/or particles may be arranged within the fibrous structure to provide the fibrous structure with two or more regions that comprise different active agents. For example, one region of the fibrous structure may comprise bleaching agents and/or surfactants and another region of the fibrous structure may comprise softening agents.

In one example, a fibrous structure according to the present invention comprises a first layer comprising a plurality of fibrous elements, for example filaments, a second layer comprising a plurality of fibrous elements, for example filaments, and a plurality of particles, for example matrix particles and/or agglomerated particles according to the present invention, positioned between (sandwiched between) the first and second layers. A similar fibrous structure can be formed by depositing a plurality of particles, for example matrix particles and/or agglomerated particles, on a surface of a first ply of fibrous structure comprising a plurality of fibrous elements and then associating a second ply of fibrous structure, for example a fibrous structure according to the present invention, comprising a plurality of fibrous elements such that the particles are positioned between (sandwiched between) the first and second plies.

In another example of the present invention, a multi-ply fibrous structure of the present invention comprises a first ply of a fibrous structure according to the present invention and a second ply of fibrous structure, for example another fibrous structure according to the present invention, associated, for example by an edge seam, with the first ply, wherein the second ply comprises a plurality of fibrous elements, for example filaments, and a plurality of particles, for example matrix particles and/or agglomerated particles, dispersed, for example randomly, in the x, y, and z axes, throughout one or both plies and/or throughout the entire multi-ply fibrous structure. In other words, the particles, for example matrix particles and/or agglomerated particles are commingled with the fibrous elements of one or both fibrous structure plies.

In one example of a fibrous structure of the present invention, the fibrous structure comprises a plurality of fibrous elements, for example filaments, and a plurality of particles, for example matrix particles and/or agglomerated particles, dispersed, for example randomly, in the x, y, and z axes, throughout the fibrous structure.

Even though the fibrous element and/or fibrous structure of the present invention are in solid form, the filament-forming composition used to make the fibrous elements of the present invention may be in the form of a liquid.

In one example, the fibrous structure comprises a plurality of identical or substantially identical from a compositional perspective of fibrous elements and/or particles according to the present invention. In another example, the fibrous structure may comprise two or more different fibrous elements and/or particles according to the present invention. Non-limiting examples of differences in the fibrous elements and/or particles may be physical differences such as differences in diameter, length, texture, shape, rigidness, elasticity, and the like; chemical differences such as crosslinking level, solubility, melting point, Tg, active agent, filament-forming material, color, level of active agent, basis weight, density, level of filament-forming material, presence of any coating on fibrous element, biodegradable or not, hydrophobic or not, contact angle, and the like; differences in whether the fibrous element and/or particle loses its physical structure when the fibrous element and/or particle is exposed to conditions of intended use; differences in whether the fibrous element's and/or particle's morphology changes when the fibrous element and/or particle is exposed to conditions of intended use; and differences in rate at which the fibrous element and/or particle releases one or more of its active agents when the fibrous element and/or particle is exposed to conditions of intended use. In one example, two or more fibrous elements and/or particles within the fibrous structure may comprise different active agents. This may be the case where the different active agents may be incompatible with one another, for example an anionic surfactant (such as a shampoo active agent) and a cationic surfactant (such as a hair conditioner active agent).

In another example, the fibrous structure may exhibit different regions, such as different regions of basis weight, density and/or caliper. In yet another example, the fibrous structure may comprise texture on one or more of its surfaces. A surface of the fibrous structure may comprise a pattern, such as a non-random, repeating pattern. The fibrous structure may be embossed with an emboss pattern. In another example, the fibrous structure may comprise apertures. The apertures may be arranged in a non-random, repeating pattern.

In another example of the present invention, the fibrous structure comprises one or more apertures and thus is an apertured fibrous structure. In one example, the fibrous structure comprises a plurality of apertures. The apertures may be arranged in a pattern, for example a repeating pattern, such as a non-random, repeating pattern, and/or a non-repeating pattern.

Apertures within the apertured fibrous structure of the present invention may be of virtually any shape and size. In one example, the apertures within the apertured fibrous structures are generally round or oblong shaped, in a regular pattern of spaced apart openings. In one example, the fibrous structure comprises two or more apertures that are spaced apart from one another at a distance of from about 0.2 mm to about 100 mm and/or from about 0.5 mm to about 10 mm Aperturing of fibrous structures, for example soluble fibrous structures, can be accomplished by any number of techniques. For example, aperturing can be accomplished by various processes involving bonding and stretching, such as those described in U.S. Pat. Nos. 3,949,127 and 5,873,868. In one embodiment, the apertures may be formed by forming a plurality of spaced, melt stabilized regions, and then ring-rolling the web to stretch the web and form apertures in the melt stabilized regions, as described in U.S. Pat. Nos. 5,628,097 and 5,916,661, both of which are hereby incorporated by reference herein. In another embodiment, apertures can be formed in a multilayer, fibrous structure configuration by the method described in U.S. Pat. Nos. 6,830,800 and 6,863,960 which are hereby incorporated herein by reference. Still another process for aperturing webs is described in U.S. Pat. No. 8,241,543 entitled "Method And Apparatus For Making An Apertured Web", which is hereby incorporated herein by reference. Non-limiting examples of processes for imparting apertures to a fibrous structure of the present invention include embossing, rodding, rotary knife aperturing, pinning, die cutting, die punching, needlepunching, knurling, crush cutting, shear cutting, pneumatic forming, hydraulic forming, laser cutting, and tufting. In one example, the fibrous structure of the present invention comprises pinning-imparted apertures. In another example, the fibrous structure of the present invention comprises rodding-imparted apertures. In another example, the fibrous structure of the present invention comprises rotary knife aperturing-imparted apertures. In still another example, the fibrous structure of the present invention may comprise apertures that have been imparted to the fibrous structure by different types of aperturing processes.

In one example, apertures may be imparted to a fibrous structure during forming of the fibrous structure on a collection device, such as a patterned belt, that has features, for example depressions and/or protrusions that impart apertures to the fibrous structure upon the fibrous elements contacting the collection device during formation.

In one example, the fibrous structure may comprise discrete regions of fibrous elements that differ from other parts of the fibrous structure.

Non-limiting examples of use of the fibrous structure of the present invention include, but are not limited to a laundry dryer substrate, washing machine substrate, washcloth, hard surface cleaning and/or polishing substrate, floor cleaning and/or polishing substrate, as a component in a battery, baby wipe, adult wipe, feminine hygiene wipe, bath tissue wipe, window cleaning substrate, oil containment and/or scavenging substrate, insect repellant substrate, swimming pool chemical substrate, food, breath freshener, deodorant, waste disposal bag, packaging film and/or wrap, wound dressing, medicine delivery, building insulation, crops and/or plant cover and/or bedding, glue substrate, skin care substrate, hair care substrate, air care substrate, water treatment substrate and/or filter, toilet bowl cleaning substrate, candy substrate, pet food, livestock bedding, teeth whitening substrates, carpet cleaning substrates, and other suitable uses of the active agents of the present invention.

The fibrous structure of the present invention may be used as is or may be coated with one or more active agents.

In one example, the fibrous structure of the present invention may exhibit an average disintegration time of less than 360 seconds (s) and/or less than 200 s and/or less than 100 s and/or less than 60 s and/or less than 30 s, and/or less than 10 s and/or less than 5 s and/or less than 2.0 s and/or less than 1.5 s and/or about 0 s and/or greater than 0 s as measured according to the Dissolution Test Method described herein.

In one example, the fibrous structure of the present invention may exhibit an average dissolution time of less than 3600 seconds (s) and/or less than 3000 s and/or less than 2400 s and/or less than 1800 s and/or less than 1200 s and/or less than 600 s and/or less than 400 s and/or less than 300 s and/or less than 200 s and/or less than 175 s and/or less than 100 s and/or less than 50 s and/or greater than 1 s as measured according to the Dissolution Test Method described herein.

In another example, the fibrous structure of the present invention exhibits an average dissolution time of less than 24 hours and/or less than 12 hours and/or less than 6 hours and/or less than 1 hour (3600 seconds) and/or less than 30 minutes and/or less than 25 minutes and/or less than 20 minutes and/or less than 15 minutes and/or less than 10 minutes and/or less than 5 minutes and/or greater than 1 second and/or greater than 5 seconds and/or greater than 10 seconds and/or greater than 30 seconds and/or greater than 1 minute as measured according to the Dissolution Test Method described herein.

In one example, the fibrous structure of the present invention may exhibit an average disintegration time per gsm of sample of about 1.0 second/gsm (s/gsm) or less, and/or about 0.5 s/gsm or less, and/or about 0.2 s/gsm or less, and/or about 0.1 s/gsm or less, and/or about 0.05 s/gsm or less, and/or about 0.03 s/gsm or less as measured according to the Dissolution Test Method described herein.

In one example, the fibrous structure of the present invention may exhibit an average dissolution time per gsm of sample of about 10 seconds/gsm (s/gsm) or less, and/or about 5.0 s/gsm or less, and/or about 3.0 s/gsm or less, and/or about 2.0 s/gsm or less, and/or about 1.8 s/gsm or less, and/or about 1.5 s/gsm or less as measured according to the Dissolution Test Method described herein.

In one example, the fibrous structure of the present invention exhibits a thickness of greater than 0.01 mm and/or greater than 0.05 mm and/or greater than 0.1 mm and/or to about 100 mm and/or to about 50 mm and/or to about 20 mm and/or to about 10 mm and/or to about 5 mm and/or to about 2 mm and/or to about 0.5 mm and/or to about 0.3 mm as measured by the Thickness Test Method described herein.

Fibrous Elements

The fibrous elements may be water-soluble or water-insoluble. In one example, the fibrous elements comprise one or more filament-forming materials. In another example, the fibrous elements comprise one or more active agents. In still another example, the fibrous elements comprise one or more filament-forming materials and one or more active agents. In another example, the fibrous elements are water-soluble fibrous elements.

The fibrous element, such as a filament and/or fiber, of the present invention comprises one or more filament-forming materials. In addition to the filament-forming materials, the fibrous element may further comprise one or more active agents that are releasable from the fibrous element, such as when the fibrous element and/or fibrous structure comprising the fibrous element is exposed to conditions of intended use. In one example, the total level of the one or more filament-forming materials present in the fibrous element is less than 80% by weight on a dry fibrous element basis and/or dry fibrous structure basis and the total level of the one or more active agents present in the fibrous element is greater than 20% by weight on a dry fibrous element basis and/or dry fibrous structure basis.

In one example, the fibrous element of the present invention comprises about 100% and/or greater than 95% and/or greater than 90% and/or greater than 85% and/or greater than 75% and/or greater than 50% by weight on a dry fibrous element basis and/or dry fibrous structure basis of one or more filament-forming materials. For example, the filament-forming material may comprise polyvinyl alcohol, starch, carboxymethylcellulose, and other suitable polymers, especially hydroxyl polymers.

In another example, the fibrous element of the present invention comprises one or more filament-forming materials and one or more active agents wherein the total level of filament-forming materials present in the fibrous element is from about 5% to less than 80% by weight on a dry fibrous element basis and/or dry fibrous structure basis and the total level of active agents present in the fibrous element is greater than 20% to about 95% by weight on a dry fibrous element basis and/or dry fibrous structure basis.

In one example, the fibrous element of the present invention comprises at least 10% and/or at least 15% and/or at least 20% and/or less than less than 80% and/or less than 75% and/or less than 65% and/or less than 60% and/or less than 55% and/or less than 50% and/or less than 45% and/or less than 40% by weight on a dry fibrous element basis and/or dry fibrous structure basis of the filament-forming materials and greater than 20% and/or at least 35% and/or at least 40% and/or at least 45% and/or at least 50% and/or at least 60% and/or less than 95% and/or less than 90% and/or less than 85% and/or less than 80% and/or less than 75% by weight on a dry fibrous element basis and/or dry fibrous structure basis of active agents.

In one example, the fibrous element of the present invention comprises at least 5% and/or at least 10% and/or at least 15% and/or at least 20% and/or less than 50% and/or less than 45% and/or less than 40% and/or less than 35% and/or less than 30% and/or less than 25% by weight on a dry fibrous element basis and/or dry fibrous structure basis of the filament-forming materials and greater than 50% and/or at least 55% and/or at least 60% and/or at least 65% and/or at least 70% and/or less than 95% and/or less than 90% and/or less than 85% and/or less than 80% and/or less than 75% by weight on a dry fibrous element basis and/or dry fibrous structure basis of active agents. In one example, the fibrous element of the present invention comprises greater than 80% by weight on a dry fibrous element basis and/or dry fibrous structure basis of active agents.

In another example, the one or more filament-forming materials and active agents are present in the fibrous element at a weight ratio of total level of filament-forming materials to active agents of 4.0 or less and/or 3.5 or less and/or 3.0 or less and/or 2.5 or less and/or 2.0 or less and/or 1.85 or less and/or less than 1.7 and/or less than 1.6 and/or less than 1.5 and/or less than 1.3 and/or less than 1.2 and/or less than 1 and/or less than 0.7 and/or less than 0.5 and/or less than 0.4 and/or less than 0.3 and/or greater than 0.1 and/or greater than 0.15 and/or greater than 0.2.

In still another example, the fibrous element of the present invention comprises from about 10% and/or from about 15% to less than 80% by weight on a dry fibrous element basis and/or dry fibrous structure basis of a filament-forming material, such as polyvinyl alcohol polymer, starch polymer, and/or carboxymethylcellulose polymer, and greater than 20% to about 90% and/or to about 85% by weight on a dry fibrous element basis and/or dry fibrous structure basis of an active agent. The fibrous element may further comprise a plasticizer, such as glycerin and/or pH adjusting agents, such as citric acid.

In yet another example, the fibrous element of the present invention comprises from about 10% and/or from about 15% to less than 80% by weight on a dry fibrous element basis and/or dry fibrous structure basis of a filament-forming material, such as polyvinyl alcohol polymer, starch polymer, and/or carboxymethylcellulose polymer, and greater than 20% to about 90% and/or to about 85% by weight on a dry fibrous element basis and/or dry fibrous structure basis of an active agent, wherein the weight ratio of filament-forming material to active agent is 4.0 or less. The fibrous element may further comprise a plasticizer, such as glycerin and/or pH adjusting agents, such as citric acid.

In even another example of the present invention, a fibrous element comprises one or more filament-forming materials and one or more active agents selected from the group consisting of: enzymes, bleaching agents, builder, chelants, sensates, dispersants, and mixtures thereof that are releasable and/or released when the fibrous element and/or fibrous structure comprising the fibrous element is exposed to conditions of intended use. In one example, the fibrous element comprises a total level of filament-forming materials of less than 95% and/or less than 90% and/or less than 80% and/or less than 50% and/or less than 35% and/or to about 5% and/or to about 10% and/or to about 20% by weight on a dry fibrous element basis and/or dry fibrous structure basis and a total level of active agents selected from the group consisting of: enzymes, bleaching agents, builder, chelants, perfumes, antimicrobials, antibacterials, antifungals, and mixtures thereof of greater than 5% and/or greater than 10% and/or greater than 20% and/or greater than 35% and/or greater than 50% and/or greater than 65% and/or to about 95% and/or to about 90% and/or to about 80% by weight on a dry fibrous element basis and/or dry fibrous structure basis. In one example, the active agent comprises one or more enzymes. In another example, the active agent comprises one or more bleaching agents. In yet another example, the active agent comprises one or more builders. In still another example, the active agent comprises one or more chelants. In still another example, the active agent comprises one or more perfumes. In even still another example, the active agent comprise one or more antimicrobials, antibacterials, and/or antifungals.

In yet another example of the present invention, the fibrous elements of the present invention may comprise active agents that may create health and/or safety concerns if they become airborne. For example, the fibrous element may be used to inhibit enzymes within the fibrous element from becoming airborne.

In one example, the fibrous elements of the present invention may be meltblown fibrous elements. In another example, the fibrous elements of the present invention may be spunbond fibrous elements. In another example, the fibrous elements may be hollow fibrous elements prior to and/or after release of one or more of its active agents.

The fibrous elements of the present invention may be hydrophilic or hydrophobic. The fibrous elements may be surface treated and/or internally treated to change the inherent hydrophilic or hydrophobic properties of the fibrous element.

In one example, the fibrous element exhibits a diameter of less than 100 µm and/or less than 75 µm and/or less than 50 µm and/or less than 25 µm and/or less than 10 µm and/or less than 5 µm and/or less than 1 µm as measured according to the Diameter Test Method described herein. In another example, the fibrous element of the present invention exhibits a diameter of greater than 1 µm as measured according to the Diameter Test Method described herein. The diameter of a fibrous element of the present invention may be used to control the rate of release of one or more active agents present in the fibrous element and/or the rate of loss and/or altering of the fibrous element's physical structure.

The fibrous element may comprise two or more different active agents. In one example, the fibrous element comprises two or more different active agents, wherein the two or more different active agents are compatible with one another. In another example, the fibrous element comprises two or more different active agents, wherein the two or more different active agents are incompatible with one another.

In one example, the fibrous element may comprise an active agent within the fibrous element and an active agent on an external surface of the fibrous element, such as an active agent coating on the fibrous element. The active agent on the external surface of the fibrous element may be the same or different from the active agent present in the fibrous element. If different, the active agents may be compatible or incompatible with one another.

In one example, one or more active agents may be uniformly distributed or substantially uniformly distributed throughout the fibrous element. In another example, one or more active agents may be distributed as discrete regions within the fibrous element. In still another example, at least one active agent is distributed uniformly or substantially uniformly throughout the fibrous element and at least one other active agent is distributed as one or more discrete regions within the fibrous element. In still yet another example, at least one active agent is distributed as one or more discrete regions within the fibrous element and at least one other active agent is distributed as one or more discrete regions different from the first discrete regions within the fibrous element.

Filament-Forming Material

The filament-forming material is any suitable material, such as a polymer or monomers capable of producing a polymer that exhibits properties suitable for making a filament, such as by a spinning process.

In one example, the filament-forming material may comprise a polar solvent-soluble material, such as an alcohol-soluble material and/or a water-soluble material.

In another example, the filament-forming material may comprise a non-polar solvent-soluble material.

In still another example, the filament-forming material may comprise a water-soluble material and be free (less than 5% and/or less than 3% and/or less than 1% and/or 0% by weight on a dry fibrous element basis and/or dry fibrous structure basis) of water-insoluble materials.

In yet another example, the filament-forming material may be a film-forming material. In still yet another example, the filament-forming material may be synthetic or of natural origin and it may be chemically, enzymatically, and/or physically modified.

In even another example of the present invention, the filament-forming material may comprise a polymer selected from the group consisting of: polymers derived from acrylic monomers such as the ethylenically unsaturated carboxylic monomers and ethylenically unsaturated monomers, polyvinyl alcohol, polyvinylformamide, polyvinylamine, polyacrylates, polymethacrylates, copolymers of acrylic acid and methyl acrylate, polyvinylpyrrolidones, polyalkylene oxides, starch and starch derivatives, pullulan, gelatin, and cellulose derivatives (for example, hydroxypropylmethyl celluloses, methyl celluloses, carboxymethyl celluloses).

In still another example, the filament-forming material may comprises a polymer selected from the group consisting of: polyvinyl alcohol, polyvinyl alcohol derivatives, starch, starch derivatives, cellulose derivatives, hemicellulose, hemicellulose derivatives, proteins, sodium alginate, hydroxypropyl methylcellulose, chitosan, chitosan derivatives, polyethylene glycol, tetramethylene ether glycol, polyvinyl pyrrolidone, hydroxymethyl cellulose, hydroxyethyl cellulose, carboxymethyl cellulose, and mixtures thereof.

In another example, the filament-forming material comprises a polymer is selected from the group consisting of: pullulan, hydroxypropylmethyl cellulose, hydroxyethyl cellulose, hydroxypropyl cellulose, polyvinyl pyrrolidone, carboxymethylcellulose, sodium alginate, xanthan gum, tragacanth gum, guar gum, acacia gum, Arabic gum, polyacrylic acid, methylmethacrylate copolymer, carboxyvinyl polymer, dextrin, pectin, chitin, levan, elsinan, collagen, gelatin, zein, gluten, soy protein, casein, polyvinyl alcohol, carboxylated polyvinyl alcohol, sulfonated polyvinyl alcohol, starch, starch derivatives, hemicellulose, hemicellulose derivatives, proteins, chitosan, chitosan derivatives, polyethylene glycol, tetramethylene ether glycol, hydroxymethyl cellulose, and mixtures thereof.

Water-Soluble Materials

Non-limiting examples of water-soluble materials include water-soluble polymers. The water-soluble polymers may be synthetic or natural original and may be chemically and/or physically modified. In one example, the polar solvent-soluble polymers exhibit a weight average molecular weight of at least 10,000 g/mol and/or at least 20,000 g/mol and/or at least 40,000 g/mol and/or at least 80,000 g/mol and/or at least 100,000 g/mol and/or at least 1,000,000 g/mol and/or at least 3,000,000 g/mol and/or at least 10,000,000 g/mol and/or at least 20,000,000 g/mol and/or to about 40,000,000 g/mol and/or to about 30,000,000 g/mol.

Non-limiting examples of water-soluble polymers include water-soluble hydroxyl polymers, water-soluble thermoplastic polymers, water-soluble biodegradable polymers, water-soluble non-biodegradable polymers and mixtures thereof. In one example, the water-soluble polymer comprises polyvinyl alcohol. In another example, the water-soluble polymer comprises starch. In yet another example, the water-soluble polymer comprises polyvinyl alcohol and starch. In yet another example, the water-soluble polymer comprises carboxymethyl cellulose. An yet in another example, the polymer comprise carboxymethyl cellulose and polyvinyl alcohol.

a. Water-soluble Hydroxyl Polymers—Non-limiting examples of water-soluble hydroxyl polymers in accordance with the present invention include polyols, such as polyvinyl alcohol, polyvinyl alcohol derivatives, polyvinyl alcohol copolymers, starch, starch derivatives, starch copolymers, chitosan, chitosan derivatives, chitosan copolymers, cellulose derivatives such as cellulose ether and ester derivatives, cellulose copolymers, hemicellulose, hemicellulose derivatives, hemicellulose copolymers, gums, arabinans, galactans, proteins, carboxymethylcellulose, and various other polysaccharides and mixtures thereof.

In one example, a water-soluble hydroxyl polymer of the present invention comprises a polysaccharide.

"Polysaccharides" as used herein means natural polysaccharides and polysaccharide derivatives and/or modified polysaccharides. Suitable water-soluble polysaccharides include, but are not limited to, starches, starch derivatives, chitosan, chitosan derivatives, cellulose derivatives, hemicellulose, hemicellulose derivatives, gums, arabinans, galactans and mixtures thereof. The water-soluble polysaccharide may exhibit a weight average molecular weight of from about 10,000 to about 40,000,000 g/mol and/or greater than 100,000 g/mol and/or greater than 1,000,000 g/mol and/or greater than 3,000,000 g/mol and/or greater than 3,000,000 to about 40,000,000 g/mol.

The water-soluble polysaccharides may comprise non-cellulose and/or non-cellulose derivative and/or non-cellulose copolymer water-soluble polysaccharides. Such non-cellulose water-soluble polysaccharides may be selected from the group consisting of: starches, starch derivatives, chitosan, chitosan derivatives, hemicellulose, hemicellulose derivatives, gums, arabinans, galactans and mixtures thereof.

In another example, a water-soluble hydroxyl polymer of the present invention comprises a non-thermoplastic polymer.

The water-soluble hydroxyl polymer may have a weight average molecular weight of from about 10,000 g/mol to about 40,000,000 g/mol and/or greater than 100,000 g/mol and/or greater than 1,000,000 g/mol and/or greater than 3,000,000 g/mol and/or greater than 3,000,000 g/mol to about 40,000,000 g/mol. Higher and lower molecular weight water-soluble hydroxyl polymers may be used in combination with hydroxyl polymers having a certain desired weight average molecular weight.

Well known modifications of water-soluble hydroxyl polymers, such as natural starches, include chemical modifications and/or enzymatic modifications. For example, natural starch can be acid-thinned, hydroxy-ethylated, hydroxy-propylated, and/or oxidized. In addition, the water-soluble hydroxyl polymer may comprise dent corn starch.

Naturally occurring starch is generally a mixture of linear amylose and branched amylopectin polymer of D-glucose units. The amylose is a substantially linear polymer of D-glucose units joined by (1,4)-α-D links. The amylopectin is a highly branched polymer of D-glucose units joined by (1,4)-α-D links and (1,6)-α-D links at the branch points. Naturally occurring starch typically contains relatively high levels of amylopectin, for example, corn starch (64-80% amylopectin), waxy maize (93-100% amylopectin), rice (83-84% amylopectin), potato (about 78% amylopectin), and wheat (73-83% amylopectin). Though all starches are potentially useful herein, the present invention is most commonly practiced with high amylopectin natural starches derived from agricultural sources, which offer the advantages of being abundant in supply, easily replenishable and inexpensive.

As used herein, "starch" includes any naturally occurring unmodified starches, modified starches, synthetic starches and mixtures thereof, as well as mixtures of the amylose or amylopectin fractions; the starch may be modified by physical, chemical, or biological processes, or combinations thereof. The choice of unmodified or modified starch for the present invention may depend on the end product desired. In one embodiment of the present invention, the starch or starch mixture useful in the present invention has an amylopectin content from about 20% to about 100%, more typically from about 40% to about 90%, even more typically from about 60% to about 85% by weight of the starch or mixtures thereof.

Suitable naturally occurring starches can include, but are not limited to, corn starch, potato starch, sweet potato starch, wheat starch, sago palm starch, tapioca starch, rice starch, soybean starch, arrow root starch, amioca starch, bracken starch, lotus starch, waxy maize starch, and high amylose corn starch. Naturally occurring starches particularly, corn starch and wheat starch, are the preferred starch polymers due to their economy and availability.

Polyvinyl alcohols herein can be grafted with other monomers to modify its properties. A wide range of monomers has been successfully grafted to polyvinyl alcohol. Non-limiting examples of such monomers include vinyl acetate, styrene, acrylamide, acrylic acid, 2-hydroxyethyl methacrylate, acrylonitrile, 1,3-butadiene, methyl methacrylate, methacrylic acid, maleic acid, itaconic acid, sodium vinylsulfonate, sodium allylsulfonate, sodium methylallyl sulfonate, sodium phenylallylether sulfonate, sodium phenylmethallylether sulfonate, 2-acrylamide-methyl propane sulfonic acid (AMPs), vinylidene chloride, vinyl chloride, vinyl amine and a variety of acrylate esters.

In one example, the water-soluble hydroxyl polymer is selected from the group consisting of: polyvinyl alcohols, hydroxymethylcelluloses, hydroxyethylcelluloses, hydroxypropylmethylcelluloses, carboxymethylcelluloses, and mixtures thereof. A non-limiting example of a suitable polyvinyl alcohol includes those commercially available from Sekisui Specialty Chemicals America, LLC (Dallas, TX) under the CELVOL® trade name Another non-limiting example of a suitable polyvinyl alcohol includes G Polymer commercially available from Nippon Ghosei. A non-limiting example of a suitable hydroxypropylmethylcellulose includes those commercially available from the Dow Chemical Company (Midland, MI) under the METHOCEL® trade name including combinations with above mentioned polyvinyl alcohols.

b. Water-soluble Thermoplastic Polymers—Non-limiting examples of suitable water-soluble thermoplastic polymers include thermoplastic starch and/or starch derivatives, polylactic acid, polyhydroxyalkanoate, polycaprolactone, polyesteramides and certain polyesters, and mixtures thereof.

The water-soluble thermoplastic polymers of the present invention may be hydrophilic or hydrophobic. The water-soluble thermoplastic polymers may be surface treated and/or internally treated to change the inherent hydrophilic or hydrophobic properties of the thermoplastic polymer.

The water-soluble thermoplastic polymers may comprise biodegradable polymers.

Any suitable weight average molecular weight for the thermoplastic polymers may be used. For example, the weight average molecular weight for a thermoplastic polymer in accordance with the present invention is greater than about 10,000 g/mol and/or greater than about 40,000 g/mol and/or greater than about 50,000 g/mol and/or less than about 500,000 g/mol and/or less than about 400,000 g/mol and/or less than about 200,000 g/mol.

Active Agents

Active agents are a class of additives that are designed and intended to provide a benefit to something other than the fibrous element and/or particle and/or fibrous structure itself, such as providing a benefit to an environment external to the fibrous element and/or particle and/or fibrous structure. Active agents may be any suitable additive that produces an intended effect under intended use conditions of the fibrous element. For example, the active agent may be selected from the group consisting of: personal cleansing and/or conditioning agents such as hair care agents such as shampoo agents and/or hair colorant agents, hair conditioning agents, skin care agents, sunscreen agents, and skin conditioning agents; laundry care and/or conditioning agents such as fabric care agents, fabric conditioning agents, fabric softening agents, fabric anti-wrinkling agents, fabric care anti-static agents, fabric care stain removal agents, soil release agents, dispersing agents, suds suppressing agents, suds boosting agents, anti-foam agents, and fabric refreshing agents; liquid and/or powder dishwashing agents (for hand dishwashing and/or automatic dishwashing machine applications), hard surface care agents, and/or conditioning agents and/or polishing agents; other cleaning and/or conditioning agents such as antimicrobial agents, antibacterial agents, antifungal agents, fabric hueing agents, perfume, bleaching agents (such as oxygen bleaching agents, hydrogen peroxide, percarbonate bleaching agents, perborate bleaching agents, chlorine bleaching agents), bleach activating agents, chelating agents, builders, lotions, brightening agents, air care agents, carpet care agents, dye transfer-inhibiting agents, clay soil removing agents, anti-redeposition agents, polymeric soil release agents, polymeric dispersing agents, alkoxylated polyamine polymers, alkoxylated polycarboxylate polymers, amphilic graft copolymers, dissolution aids, buffering systems, water-softening agents, water-hardening agents, pH adjusting agents, enzymes, flocculating agents, effervescent agents, preservatives, cosmetic agents, make-up removal agents, lathering agents, deposition aid agents, coacervate-forming agents, clays, thickening agents, latexes, silicas, drying agents, odor control agents, antiperspirant agents, cooling agents, warming agents, absorbent gel agents, anti-inflammatory agents, dyes, pigments, acids, and bases; liquid treatment active agents; agricultural active agents; industrial active agents; ingestible active agents such as medicinal agents, oral care agents, such as teeth whitening agents, tooth care agents, mouthwash agents, and periodontal gum care agents, edible agents, dietary agents, vitamins, minerals; water-treatment agents such as water clarifying and/or water disinfecting agents, and mixtures thereof.

Non-limiting examples of suitable cosmetic agents, skin care agents, skin conditioning agents, hair care agents, and hair conditioning agents are described in CTFA Cosmetic Ingredient Handbook, Second Edition, The Cosmetic, Toiletries, and Fragrance Association, Inc. 1988, 1992.

One or more classes of chemicals may be useful for one or more of the active agents listed above. For example, surfactants may be used for any number of the active agents described above. Likewise, bleaching agents may be used for fabric care, hard surface cleaning, dishwashing and even teeth whitening. Therefore, one of ordinary skill in the art will appreciate that the active agents will be selected based upon the desired intended use of the fibrous element and/or particle and/or fibrous structure made therefrom.

For example, if the fibrous element and/or particle and/or fibrous structure made therefrom is to be used for hair care and/or conditioning then one or more suitable surfactants, such as a lathering surfactant could be selected to provide the desired benefit to a consumer when exposed to conditions of intended use of the fibrous element and/or particle and/or fibrous structure incorporating the fibrous element and/or particle.

In one example, if the fibrous element and/or particle and/or fibrous structure made therefrom is designed or intended to be used for laundering clothes in a laundry operation, then one or more suitable surfactants and/or enzymes and/or builders and/or perfumes and/or suds suppressors and/or bleaching agents could be selected to provide the desired benefit to a consumer when exposed to conditions of intended use of the fibrous element and/or particle and/or fibrous structure incorporating the fibrous element and/or particle. In another example, if the fibrous element and/or particle and/or fibrous structure made therefrom is designed to be used for laundering clothes in a laundry operation and/or cleaning dishes in a dishwashing operation, then the fibrous element and/or particle and/or fibrous structure may comprise a laundry detergent composition or dishwashing detergent composition or active agents used in such compositions.

In one example, the active agent comprises a non-perfume active agent. In another example, the active agent comprises a non-surfactant active agent. In still another example, the active agent comprises a non-ingestible active agent, in other words an active agent other than an ingestible active agent.

Surfactants

Non-limiting examples of suitable surfactants include anionic surfactants, cationic surfactants, nonionic surfactants, zwitterionic surfactants, amphoteric surfactants, and mixtures thereof. Co-surfactants may also be included in the fibrous elements and/or particles. For fibrous elements and/or particles designed for use as laundry detergents and/or dishwashing detergents, the total level of surfactants should be sufficient to provide cleaning including stain and/or odor removal, and generally ranges from about 0.5% to about 95%. Further, surfactant systems comprising two or more surfactants that are designed for use in fibrous elements and/or particles for laundry detergents and/or dishwashing detergents may include all-anionic surfactant systems, mixed-type surfactant systems comprising anionic-nonionic surfactant mixtures, or nonionic-cationic surfactant mixtures or low-foaming nonionic surfactants.

The surfactants herein can be linear or branched. In one example, suitable linear surfactants include those derived from agrochemical oils such as coconut oil, palm kernel oil, soybean oil, or other vegetable-based oils.

a. Anionic Surfactants

Non-limiting examples of suitable anionic surfactants include alkyl sulfates, alkyl ether sulfates, branched alkyl sulfates, branched alkyl alkoxylates, branched alkyl alkoxylate sulfates, mid-chain branched alkyl aryl sulfonates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, sodium lauroyl glutamate, and combinations thereof.

Alkyl sulfates and alkyl ether sulfates suitable for use herein include materials with the respective formula $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium and triethanolamine Other suitable anionic surfactants are described in McCutcheon's Detergents and Emulsifiers, North American Edition (1986), Allured Publishing Corp. and McCutcheon's, Functional Materials, North American Edition (1992), Allured Publishing Corp.

In one example, anionic surfactants useful in the fibrous elements and/or particles of the present invention include $C_9$-$C_{15}$ alkyl benzene sulfonates (LAS), $C_8$-$C_{20}$ alkyl ether sulfates, for example alkyl poly(ethoxy) sulfates, $C_8$-$C_{20}$ alkyl sulfates, and mixtures thereof. Other anionic surfactants include methyl ester sulfonates (MES), secondary alkane sulfonates, methyl ester ethoxylates (MEE), sulfonated estolides, and mixtures thereof.

In another example, the anionic surfactant is selected from the group consisting of: $C_{11}$-$C_{18}$ alkyl benzene sulfonates ("LAS") and primary, branched-chain and random $C_{10}$-$C_{20}$ alkyl sulfates ("AS"), $C_{10}$-$C_{18}$ secondary (2,3) alkyl sulfates of the formula $CH_3(CH_2)_x(CHOSO_3^-M^+)CH_3$ and $CH_3(CH_2)_y(CHOSO_3^-M^+)CH_2CH_3$ where x and (y+1) are integers of at least about 7, preferably at least about 9, and M is a water-solubilizing cation, especially sodium, unsaturated sulfates such as oleyl sulfate, the $C_{10}$-$C_{18}$ alpha-sulfonated fatty acid esters, the $C_{10}$-$C_{18}$ sulfated alkyl polyglycosides, the $C_{10}$-$C_{18}$ alkyl alkoxy sulfates ("AE$_x$S") wherein x is from 1-30, and $C_{10}$-$C_{18}$ alkyl alkoxy carboxylates, for example comprising 1-5 ethoxy units, mid-chain branched alkyl sulfates as discussed in U.S. Pat. No. 6,020,303 and U.S. Pat. No. 6,060,443; mid-chain branched alkyl alkoxy sulfates as discussed in U.S. Pat. No. 6,008,181 and U.S. Pat. No. 6,020,303; modified alkylbenzene sulfonate (MLAS) as discussed in WO 99/05243, WO 99/05242 and WO 99/05244; methyl ester sulfonate (MES); and alpha-olefin sulfonate (AOS).

b. Cationic Surfactants

Non-limiting examples of suitable cationic surfactants include, but are not limited to, those having the formula (I):

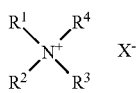

in which $R^1$, $R^2$, $R^3$, and $R^4$ are each independently selected from (a) an aliphatic group of from 1 to 26 carbon atoms, or (b) an aromatic, alkoxy, polyoxyalkylene, alkylcarboxy, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate, nitrate, sulphate, and alkylsulphate radicals. In one example, the alkylsulphate radical is methosulfate and/or ethosulfate.

Suitable quaternary ammonium cationic surfactants of general formula (I) may include cetyltrimethylammonium chloride, behenyltrimethylammonium chloride (BTAC), stearyltrimethylammonium chloride, cetylpyridinium chloride, octadecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, didecyldimehtylammonium chloride, dioctadecyldimethylammonium chloride, distearyldimethylammonium chloride, tallowtrimethylammonium chloride, cocotrimethylammonium chloride, 2-ethylhexylstearyldimethylammonium chloride, dipalmitoylethyldimethylammonium chloride, ditallowoylethyldimethylammonium chloride, distearoylethyldimethylammonium methosulfate, PEG-2 oleylammonium chloride and salts of these, where the chloride is replaced by halogen, (e.g., bromide), acetate, citrate, lactate, glycolate, phosphate nitrate, sulphate, or alkylsulphate.

Non-limiting examples of suitable cationic surfactants are commercially available under the trade names ARQUAD® from Akzo Nobel Surfactants (Chicago, Ill.).

In one example, suitable cationic surfactants include quaternary ammonium surfactants, for example that have up to 26 carbon atoms include: alkoxylate quaternary ammonium (AQA) surfactants as discussed in U.S. Pat. No. 6,136,769; dimethyl hydroxyethyl quaternary ammonium as discussed in U.S. Pat. No. 6,004,922; dimethyl hydroxyethyl lauryl ammonium chloride; polyamine cationic surfactants as discussed in WO 98/35002, WO 98/35003, WO 98/35004, WO 98/35005, and WO 98/35006; cationic ester surfactants as discussed in U.S. Pat. Nos. 4,228,042, 4,239,660 4,260,529 and U.S. Pat. No. 6,022,844; and amino surfactants as discussed in U.S. Pat. No. 6,221,825 and WO 00/47708, for example amido propyldimethyl amine (APA).

In one example the cationic ester surfactants are hydrolyzable under the conditions of a laundry wash.

c. Nonionic Surfactants

Non-limiting examples of suitable nonionic surfactants include alkoxylated alcohols (AE's) and alkyl phenols, polyhydroxy fatty acid amides (PFAA's), alkyl polyglycosides (APG's), $C_{10}$-$C_{18}$ glycerol ethers, and the like.

In one example, non-limiting examples of nonionic surfactants useful in the present invention include: $C_{12}$-$C_{18}$ alkyl ethoxylates, such as, NEODOL® nonionic surfactants from Shell; $C_6$-$C_{12}$ alkyl phenol alkoxylates wherein the alkoxylate units are a mixture of ethyleneoxy and propyleneoxy units; $C_{12}$-$C_{15}$ alcohol and $C_6$-$C_{12}$ alkyl phenol condensates with ethylene oxide/propylene oxide block alkyl polyamine ethoxylates such as PLURONIC® from BASF; $C_{14}$-$C_{22}$ mid-chain branched alcohols, BA, as discussed in U.S. Pat. No. 6,150,322; $C_{14}$-$C_{22}$ mid-chain branched alkyl alkoxylates, $BAE_x$, wherein x is from 1-30, as discussed in U.S. Pat. No. 6,153,577, U.S. Pat. No. 6,020,303 and U.S. Pat. No. 6,093,856; alkylpolysaccharides as discussed in U.S. Pat. No. 4,565,647 Llenado, issued Jan. 26, 1986; specifically alkylpolyglycosides as discussed in U.S. Pat. No. 4,483,780 and U.S. Pat. No. 4,483,779; polyhydroxy detergent acid amides as discussed in U.S. Pat. No. 5,332,528; and ether capped poly(oxyalkylated) alcohol surfactants as discussed in U.S. Pat. No. 6,482,994 and WO 01/42408.

Examples of commercially available nonionic surfactants suitable for the present invention include: Tergitol® 15-S-9 (the condensation product of $C_{11}$-$C_{15}$ linear alcohol with 9 moles ethylene oxide) and Tergitol® 24-L-6 NMW (the condensation product of $C_{12}$-$C_{14}$ primary alcohol with 6 moles ethylene oxide with a narrow molecular weight distribution), both marketed by Dow Chemical Company; Neodol® 45-9 (the condensation product of $C_{14}$-$C_{15}$ linear alcohol with 9 moles of ethylene oxide), Neodol® 23-3 (the condensation product of $C_{12}$-$C_{13}$ linear alcohol with 3 moles of ethylene oxide), Neodol® 45-7 (the condensation product of $C_{14}$-$C_{15}$ linear alcohol with 7 moles of ethylene oxide) and Neodol® 45-5 (the condensation product of $C_{14}$-$C_{15}$ linear alcohol with 5 moles of ethylene oxide) marketed by Shell Chemical Company; Kyro® EOB (the condensation product of $C_{13}$-$C_{15}$ alcohol with 9 moles ethylene oxide), marketed by The Procter & Gamble Company; and Genapol LA O3O or O5O (the condensation product of $C_{12}$-$C_{14}$ alcohol with 3 or 5 moles of ethylene oxide) marketed by Clariant. The nonionic surfactants may exhibit an HLB range of from about 8 to about 17 and/or from about 8 to about 14. Condensates with propylene oxide and/or butylene oxides may also be used.

Polyethylene, polypropylene, and polybutylene oxide condensates of alkyl phenols are also suitable for use as a nonionic surfactant in the present invention. These compounds include the condensation products of alkyl phenols having an alkyl group containing from about 6 to about 14 carbon atoms, in either a straight-chain or branched-chain configuration with the alkylene oxide. Commercially available nonionic surfactants of this type include Igepal® CO-630, marketed by Solvay-Rhodia; and Triton® X-45, X-114, X-100 and X-102, all marketed by the Dow Chemical Company.

For automatic dishwashing applications, low foaming nonionic surfactants may be used. Suitable low foaming nonionic surfactants are disclosed in U.S. Pat. No. 7,271,138 col. 7, line 10 to col. 7, line 60.

Examples of other suitable nonionic surfactants are the commercially-available Pluronic® surfactants, marketed by BASF, the commercially available Tetronic® compounds, marketed by BASF, and the commercially available Plurafac® surfactants, marketed by BASF.

d. Zwitterionic Surfactants

Non-limiting examples of zwitterionic or ampholytic surfactants include: derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 at column 19, line 38 through column 22, line 48, for examples of zwitterionic surfactants; betaines, including alkyl dimethyl betaine and cocodimethyl amidopropyl betaine, $C_8$ to $C_{18}$ (for example from $C_{12}$ to $C_{18}$) amine oxides and sulfo and hydroxy betaines, such as N-alkyl-N,N-dimethylammino-1-propane sulfonate where the alkyl group can be $C_8$ to $C_{18}$ and in certain embodiments from $C_{10}$ to $C_{14}$.

e. Amphoteric Surfactants

Non-limiting examples of amphoteric surfactants include: aliphatic derivatives of secondary or tertiary amines, or aliphatic derivatives of heterocyclic secondary and tertiary amines in which the aliphatic radical can be straight- or branched-chain and mixtures thereof. One of the aliphatic substituents may contain at least about 8 carbon atoms, for example from about 8 to about 18 carbon atoms, and at least one contains an anionic water-solubilizing group, e.g. carboxy, sulfonate, sulfate. See U.S. Pat. No. 3,929,678 at column 19, lines 18-35, for suitable examples of amphoteric surfactants.

Perfumes

One or more perfume and/or perfume raw materials such as accords and/or notes may be incorporated into one or more of the fibrous elements and/or particles of the present invention. The perfume may comprise a perfume ingredient selected from the group consisting of: aldehyde perfume ingredients, ketone perfume ingredients, and mixtures thereof.

One or more perfumes and/or perfumery ingredients may be included in the fibrous elements and/or particles of the present invention. A wide variety of natural and synthetic chemical ingredients useful as perfumes and/or perfumery ingredients include but not limited to aldehydes, ketones, esters, and mixtures thereof. Also included are various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. In one example, a finished perfume typically comprises from about 0.01% to about 2% by weight on a dry fibrous element basis and/or a dry particle basis and/or dry fibrous structure basis.

Antimicrobials, Antibacterials & Antifungals

In an embodiment, pyridinethione particulates are suitable antimicrobial active agents for use in the present invention. In an embodiment, the antimicrobial active agent is a 1-hydroxy-2-pyridinethione salt and is in particulate form. In an embodiment, the concentration of pyridinethione particulate ranges from about 0.01 wt % to about 5 wt %, or from about 0.1 wt % to about 3 wt %, or from about 0.1 wt % to about 2 wt %, by weight of the dry fibrous element and/or dry particle and/or dry fibrous structure of the present invention. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns as measured according to the Median Particle Size Test Method described herein. Salts formed from other cations, such as sodium, may also be suitable. Pyridinethione actives are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

In another embodiment, the antibacterial is chosen from triclosan, triclocarban, chlorhexidine, metronitazole and mixtures thereof.

In an embodiment, in addition to the antimicrobial active selected from polyvalent metal salts of pyrithione, the composition can further include one or more anti-fungal and/or anti-microbial actives. In an embodiment, the anti-microbial active is selected from the group consisting of: coal tar, sulfur, azoles, selenium sulphide, particulate sulphur, keratolytic agents, charcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof.

Filament-Forming Composition

The fibrous elements of the present invention are made from a filament-forming composition. The filament-forming composition is a polar-solvent-based composition. In one example, the filament-forming composition is an aqueous composition comprising one or more filament-forming materials and one or more active agents.

The filament-forming composition of the present invention may have a shear viscosity as measured according to the Shear Viscosity Test Method described herein of from about 1 Pascal·Seconds to about 25 Pascal·Seconds and/or from about 2 Pascal·Seconds to about 20 Pascal·Seconds and/or from about 3 Pascal·Seconds to about 10 Pascal·Seconds, as measured at a shear rate of 3,000 $sec^{-1}$ and at the processing temperature (50° C. to 100° C.).

The filament-forming composition may be processed at a temperature of from about 50° C. to about 100° C. and/or from about 65° C. to about 95° C. and/or from about 70° C. to about 90° C. when making fibrous elements from the filament-forming composition.

In one example, the filament-forming composition may comprise at least 20% and/or at least 30% and/or at least 40% and/or at least 45% and/or at least 50% to about 90% and/or to about 85% and/or to about 80% and/or to about 75% by weight of one or more filament-forming materials, one or more active agents, and mixtures thereof. The filament-forming composition may comprise from about 10% to about 80% by weight of a polar solvent, such as water.

In one example, non-volatile components of the filament-forming composition may comprise from about 20% and/or 30% and/or 40% and/or 45% and/or 50% to about 75% and/or 80% and/or 85% and/or 90% by weight based on the total weight of the filament-forming composition. The non-volatile components may be composed of filament-forming materials, such as backbone polymers, active agents and combinations thereof. Volatile components of the filament-forming composition will comprise the remaining percentage and range from 10% to 80% by weight based on the total weight of the filament-forming composition.

In a fibrous element spinning process, the fibrous elements need to have initial stability as they leave the spinning die. Capillary Number is used to characterize this initial stability criterion. At the conditions of the die, the Capillary Number should be at least 1 and/or at least 3 and/or at least 4 and/or at least 5.

In one example, the filament-forming composition exhibits a Capillary Number of from at least 1 to about 50 and/or at least 3 to about 50 and/or at least 5 to about 30 such that the filament-forming composition can be effectively polymer processed into a fibrous element.

"Polymer processing" as used herein means any spinning operation and/or spinning process by which a fibrous element comprising a processed filament-forming material is formed from a filament-forming composition. The spinning operation and/or process may include spun bonding, melt blowing, electro-spinning, rotary spinning, continuous filament producing and/or tow fiber producing operations/processes. A "processed filament-forming material" as used herein means any filament-forming material that has undergone a melt processing operation and a subsequent polymer processing operation resulting in a fibrous element.

The Capillary number is a dimensionless number used to characterize the likelihood of this droplet breakup. A larger capillary number indicates greater fluid stability upon exiting the die. The Capillary number is defined as follows:

$$Ca = \frac{V * \eta}{\sigma}$$

V is the fluid velocity at the die exit (units of Length per Time),
$\eta$ is the fluid viscosity at the conditions of the die (units of Mass per Length*Time),
$\sigma$ is the surface tension of the fluid (units of mass per Time$^2$).
When velocity, viscosity, and surface tension are expressed in a set of consistent units, the resulting Capillary number will have no units of its own; the individual units will cancel out.

The Capillary number is defined for the conditions at the exit of the die. The fluid velocity is the average velocity of the fluid passing through the die opening. The average velocity is defined as follows:

$$V = \frac{Vol'}{Area}$$

Vol'=volumetric flowrate (units of Length$^3$ per Time),
Area=cross-sectional area of the die exit (units of Length$^2$).
When the die opening is a circular hole, then the fluid velocity can be defined as $$V = \frac{Vol'}{\pi * R^2}$$

R is the radius of the circular hole (units of length).

The fluid viscosity will depend on the temperature and may depend of the shear rate. The definition of a shear thinning fluid includes a dependence on the shear rate. The surface tension will depend on the makeup of the fluid and the temperature of the fluid.

In one example, the filament-forming composition may comprise one or more release agents and/or lubricants. Non-limiting examples of suitable release agents and/or lubricants include fatty acids, fatty acid salts, fatty alcohols, fatty esters, sulfonated fatty acid esters, fatty amine acetates and fatty amides, silicones, aminosilicones, fluoropolymers and mixtures thereof.

In one example, the filament-forming composition may comprise one or more antiblocking and/or detackifying agents. Non-limiting examples of suitable antiblocking and/or detackifying agents include starches, modified starches, crosslinked polyvinylpyrrolidone, crosslinked cellulose, microcrystalline cellulose, silica, metallic oxides, calcium carbonate, talc and mica.

Active agents of the present invention may be added to the filament-forming composition prior to and/or during fibrous element formation and/or may be added to the fibrous element after fibrous element formation. For example, a perfume active agent may be applied to the fibrous element and/or fibrous structure comprising the fibrous element after the fibrous element and/or fibrous structure according to the present invention are formed. In another example, an enzyme active agent may be applied to the fibrous element and/or fibrous structure comprising the fibrous element after the fibrous element and/or fibrous structure according to the present invention are formed. In still another example, one or more particles, which may not be suitable for passing through the spinning process for making the fibrous element, may be applied to the fibrous element and/or fibrous structure comprising the fibrous element after the fibrous element and/or fibrous structure according to the present invention are formed.

Method for Making Fibrous Elements

The fibrous elements of the present invention may be made by any suitable process. A non-limiting example of a suitable process for making the fibrous elements is described below.

In one example, a method for making a fibrous element according to the present invention comprises the steps of:
a. providing a filament-forming composition comprising one or more filament-forming materials, and optionally one or more active agents; and
b. spinning the filament-forming composition, such as via a spinning die, into one or more fibrous elements, such as filaments, comprising the one or more filament-forming materials and optionally, the one or more active agents. The one or more active agents may be releasable from the fibrous element when exposed to conditions of intended use. The total level of the one or more filament-forming materials present in the fibrous element, when active agents are present therein, may be less than 80% and/or less than 70% and/or less than 65% and/or 50% or less by weight on a dry fibrous element basis and/or dry fibrous structure basis and the total level of the one or more active agents, when present in the fibrous element may be greater than 20% and/or greater than 35% and/or 50% or greater 65% or greater and/or 80% or greater by weight on a dry fibrous element basis and/or dry fibrous structure basis.

The spinning die may comprise a plurality of fibrous element-forming holes that include a melt capillary encircled by a concentric attenuation fluid hole through which a fluid, such as air, passes to facilitate attenuation of the filament-forming composition into a fibrous element as it exits the fibrous element-forming hole.

In one example, during the spinning step, any volatile solvent, such as water, present in the filament-forming composition is removed, such as by drying, as the fibrous element is formed. In one example, greater than 30% and/or greater than 40% and/or greater than 50% of the weight of the filament-forming composition's volatile solvent, such as water, is removed during the spinning step, such as by drying the fibrous element being produced.

The filament-forming composition may comprise any suitable total level of filament-forming materials and any suitable level of active agents so long as the fibrous element produced from the filament-forming composition comprises a total level of filament-forming materials in the fibrous element of from about 5% to 50% or less by weight on a dry fibrous element basis and/or dry particle basis and/or dry fibrous structure basis and a total level of active agents in the fibrous element of from 50% to about 95% by weight on a dry fibrous element basis and/or dry particle basis and/or dry fibrous structure basis.

In one example, the filament-forming composition may comprise any suitable total level of filament-forming materials and any suitable level of active agents so long as the fibrous element produced from the filament-forming composition comprises a total level of filament-forming materials in the fibrous element and/or particle of from about 5% to 50% or less by weight on a dry fibrous element basis and/or dry particle basis and/or dry fibrous structure basis and a total level of active agents in the fibrous element and/or particle of from 50% to about 95% by weight on a dry fibrous element basis and/or dry particle basis and/or dry fibrous structure basis, wherein the weight ratio of filament-forming material to total level of active agents is 1 or less.

In one example, the filament-forming composition comprises from about 1% and/or from about 5% and/or from about 10% to about 50% and/or to about 40% and/or to about 30% and/or to about 20% by weight of the filament-forming composition of filament-forming materials; from about 1% and/or from about 5% and/or from about 10% to about 50% and/or to about 40% and/or to about 30% and/or to about 20% by weight of the filament-forming composition of active agents; and from about 20% and/or from about 25% and/or from about 30% and/or from about 40% and/or to about 80% and/or to about 70% and/or to about 60% and/or to about 50% by weight of the filament-forming composition of a volatile solvent, such as water. The filament-forming composition may comprise minor amounts of other active agents, such as less than 10% and/or less than 5% and/or less than 3% and/or less than 1% by weight of the filament-forming composition of plasticizers, pH adjusting agents, and other active agents.

The filament-forming composition is spun into one or more fibrous elements and/or particles by any suitable spinning process, such as meltblowing, spunbonding, electro-spinning, and/or rotary spinning In one example, the filament-forming composition is spun into a plurality of fibrous elements and/or particles by meltblowing. For example, the filament-forming composition may be pumped from a tank to a meltblown spinnerette. Upon exiting one or more of the filament-forming holes in the spinnerette, the filament-forming composition is attenuated with air to create one or more fibrous elements and/or particles. The fibrous elements and/or particles may then be dried to remove any remaining solvent used for spinning, such as the water.

The fibrous elements and/or particles of the present invention may be collected on a belt, such as a patterned belt, for example a molding member, to form a fibrous structure comprising the fibrous elements and/or particles.

Figure 4:
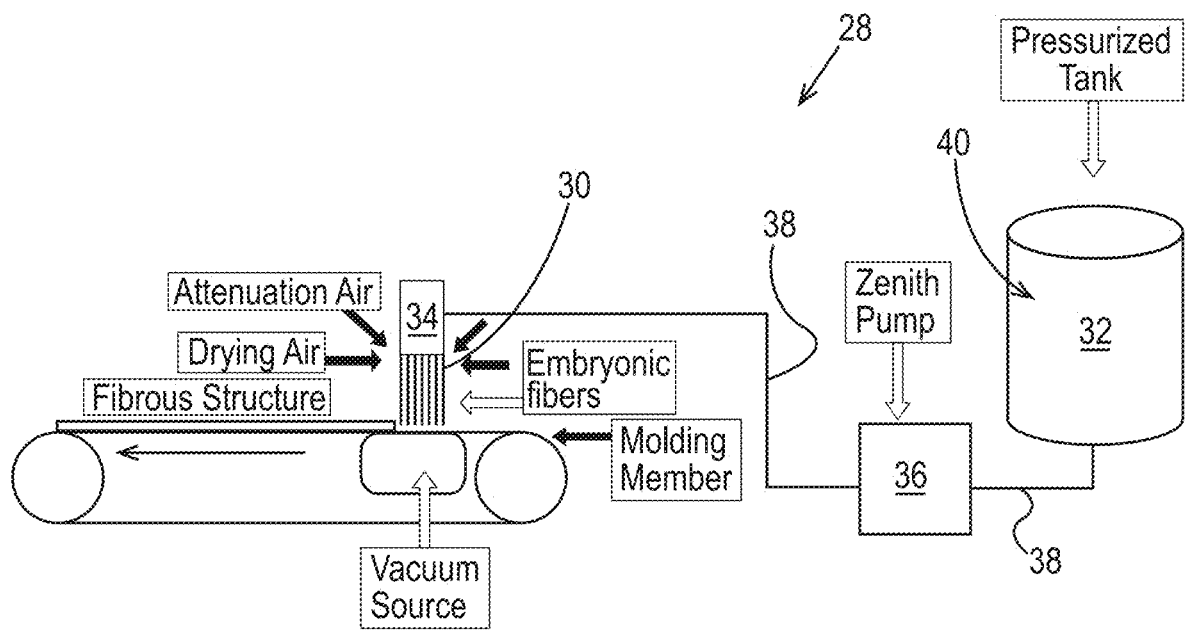
FIG. 4 is a schematic representation of an example of a process for making fibrous elements of the present invention.
Figure 5:
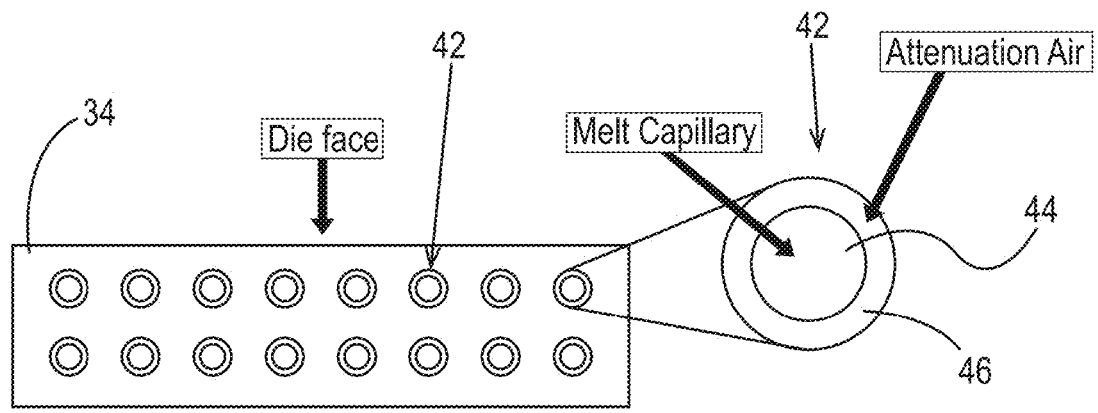
FIG. 5 is a schematic representation of an example of a die with a magnified view used in the process of FIG. 4.

In one example, as shown in FIGS. 4 and 5. a method 28 for making a fibrous element 30 according to the present invention comprises the steps of:

a. providing a filament-forming composition 32 comprising one or more filament-forming materials, and optionally one or more active agents; and b. spinning the filament-forming composition 32, such as via a spinning die 34 facilitated by a pump 36, pipes 38 and pressurized tank 40, into one or more fibrous elements 30, such as filaments, comprising the one or more filament-forming materials and optionally, the one or more active agents. The one or more active agents may be releasable from the fibrous element when exposed to conditions of intended use. The total level of the one or more filament-forming materials present in the fibrous element 30, when active agents are present therein, may be less than 80% and/or less than 70% and/or less than 65% and/or 50% or less by weight on a dry fibrous element basis and/or dry fibrous structure basis and the total level of the one or more active agents, when present in the fibrous element may be greater than 20% and/or greater than 35% and/or 50% or greater 65% or greater and/or 80% or greater by weight on a dry fibrous element basis and/or dry fibrous structure basis.

As shown in FIG. 4, the spinning die 34 may comprise a plurality of fibrous element-forming holes 42 that include a melt capillary 44 encircled by a concentric attenuation fluid hole 46 through which a fluid, such as air, passes to facilitate attenuation of the filament-forming composition 32 into a fibrous element 30 as it exits the fibrous element-forming hole 42.

In one example, during the spinning step, any volatile solvent, such as water, present in the filament-forming composition 32 is removed, such as by drying, as the fibrous element 30 is formed. In one example, greater than 30% and/or greater than 40% and/or greater than 50% of the weight of the filament-forming composition's volatile solvent, such as water, is removed during the spinning step, such as by drying the fibrous element being produced.

The filament-forming composition may comprise any suitable total level of filament-forming materials and any suitable level of active agents so long as the fibrous element produced from the filament-forming composition comprises a total level of filament-forming materials in the fibrous element of from about 5% to 50% or less by weight on a dry fibrous element basis and/or dry particle basis and/or dry fibrous structure basis and a total level of active agents in the fibrous element of from 50% to about 95% by weight on a dry fibrous element basis and/or dry particle basis and/or dry fibrous structure basis.

In one example, the filament-forming composition may comprise any suitable total level of filament-forming materials and any suitable level of active agents so long as the fibrous element produced from the filament-forming composition comprises a total level of filament-forming materials in the fibrous element and/or particle of from about 5% to 50% or less by weight on a dry fibrous element basis and/or dry particle basis and/or dry fibrous structure basis and a total level of active agents in the fibrous element and/or particle of from 50% to about 95% by weight on a dry fibrous element basis and/or dry particle basis and/or dry fibrous structure basis, wherein the weight ratio of filament-forming material to total level of active agents is 1 or less.

In one example, the filament-forming composition comprises from about 1% and/or from about 5% and/or from about 10% to about 50% and/or to about 40% and/or to about 30% and/or to about 20% by weight of the filament-forming composition of filament-forming materials; from about 1% and/or from about 5% and/or from about 10% to about 50% and/or to about 40% and/or to about 30% and/or to about 20% by weight of the filament-forming composition of active agents; and from about 20% and/or from about 25% and/or from about 30% and/or from about 40% and/or to about 80% and/or to about 70% and/or to about 60% and/or to about 50% by weight of the filament-forming composition of a volatile solvent, such as water. The filament-forming composition may comprise minor amounts of other active agents, such as less than 10% and/or less than 5% and/or less than 3% and/or less than 1% by weight of the filament-forming composition of plasticizers, pH adjusting agents, and other active agents.

The filament-forming composition is spun into one or more fibrous elements and/or particles by any suitable spinning process, such as meltblowing, spunbonding, electro-spinning, and/or rotary spinning In one example, the filament-forming composition is spun into a plurality of fibrous elements and/or particles by meltblowing. For example, the filament-forming composition may be pumped from a tank to a meltblown spinnerette. Upon exiting one or more of the filament-forming holes in the spinnerette, the filament-forming composition is attenuated with air to create one or more fibrous elements and/or particles. The fibrous elements and/or particles may then be dried to remove any remaining solvent used for spinning, such as the water.

The fibrous elements and/or particles of the present invention may be collected on a belt, such as a patterned belt, for example a molding member, to form a fibrous structure comprising the fibrous elements and/or particles.

Method for Making Fibrous Structures

A fibrous structure of the present invention may be made by spinning a filament-forming composition from a spinning die, to form a plurality of fibrous elements, such as filaments, and then associating one or more particles, for example one or more matrix particles and/or agglomerated particles, provided by a particle source, for example a sifter or an airlaid forming head. The particles, for example matrix particles and/or agglomerated particles, may be dispersed within the fibrous elements. The mixture of particles and fibrous elements may be collected on a collection belt, such as a patterned collection belt that imparts a texture, such as a three-dimensional texture to at least one surface of the fibrous structure.

In one example of a method for making a fibrous structure of the present invention, the method comprises the steps of forming a first layer of a plurality of fibrous elements, for example filaments. Depositing one or more particles, for example matrix particles and/or agglomerated particles, onto a surface of the first layer from a particle source. Then forming a second layer of a plurality of fibrous elements, for example filaments, produced for example from a spinning die on top of the particles such that the particles are positioned between (sandwiched between) the first layer and the second layer.

In another example of a method for making a fibrous structure of the present invention, the method comprises the steps of producing a plurality of fibrous elements, for example from a spinning die, and commingling a plurality of particles, for example matrix particles and/or agglomerated particles, with the fibrous elements to form a co-formed fibrous structure.

Figure 6:
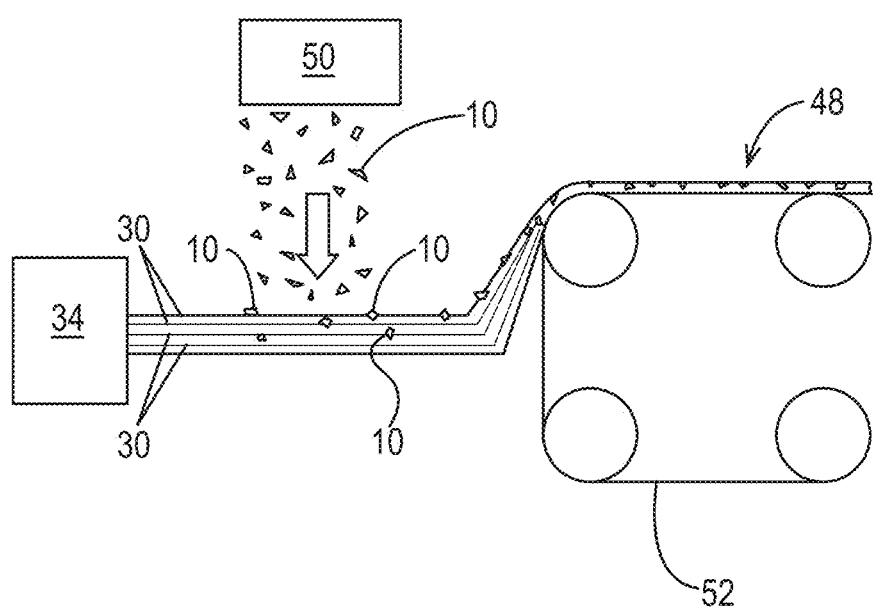
FIG. 6 is a schematic representation of an example of a process for making a fibrous structure according to the present invention.

In one example as shown in FIG. 6, a fibrous structure 48 of the present invention may be made by spinning a filament-forming composition 32 from a spinning die 34, as described in FIGS. 4 and 5, to form a plurality of fibrous elements 30, such as filaments, and then associating one or more matrix particles 10 and/or agglomerated particles provided by a matrix particle source 50, for example a sifter or an airlaid forming head. The matrix particles 10 may be dispersed within the fibrous elements 30. The mixture of matrix particles 10 and fibrous elements 30 may be collected on a collection belt 52, such as a patterned collection belt that imparts a texture, such as a three-dimensional texture to at least one surface of the fibrous structure 48.

In one example, the fibrous structure 48 may be exhibit any suitable basis weight, for example from about 100 gsm to about 5000 gsm and/or from about 250 gsm to about 3000 gsm and/or from about 500 gsm to about 2000 gsm. The fibrous elements 32 within the fibrous structure 28 may be present at any suitable basis weight, for example from about 10 gsm to about 500 gsm and/or from about 20 gsm to about 400 gsm and/or from about 100 gsm to about 300 gsm. The matrix particles 36 within the fibrous structure 28 may be present at any suitable basis weight, for example from about 100 gsm to about 4000 gsm and/or from about 250 gsm to about 3000 gsm and/or from about 500 gsm to about 2000 gsm.

Figure 7:
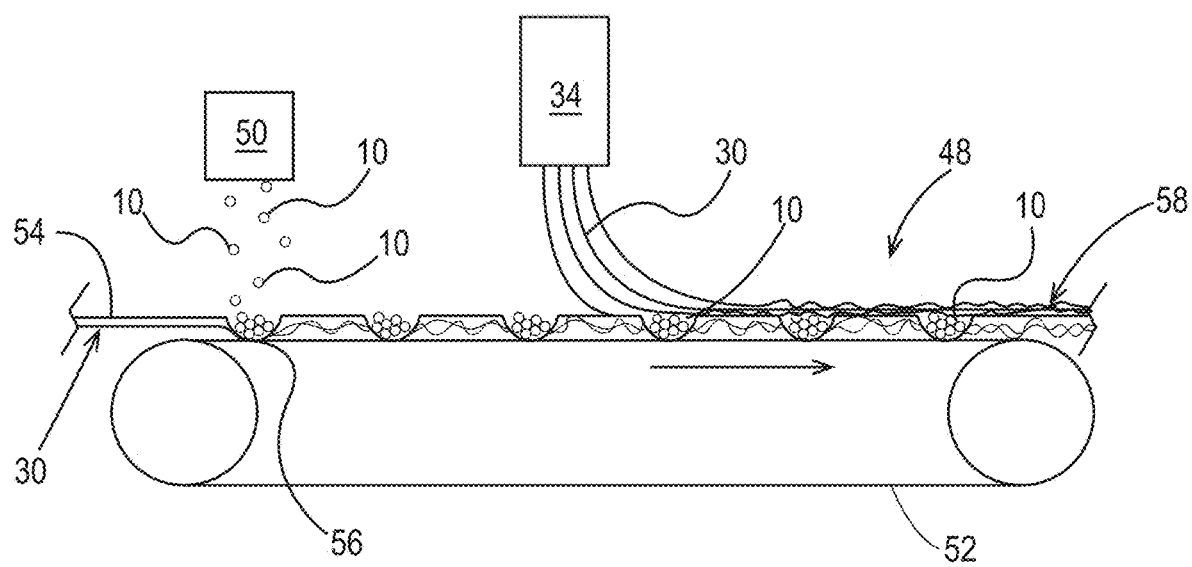
FIG. 7 is a schematic representation of another example of a process for making a fibrous structure according to the present invention.

FIG. 7 illustrates another example of a method for making a fibrous structure 48 according to the present invention. The method comprises the steps of forming a first layer 54 of a plurality of fibrous elements 30 such that pockets 56 are formed in a surface of the first layer 54. One or more matrix particles 10 are deposited into the pockets 56 from a matrix particle source 50. A second layer 58 comprising a plurality of fibrous elements 30 produced from a spinning die 34 are then formed on the surface of the first layer 54 such that the matrix particles 10 are entrapped in the pockets 56.

Figure 8:
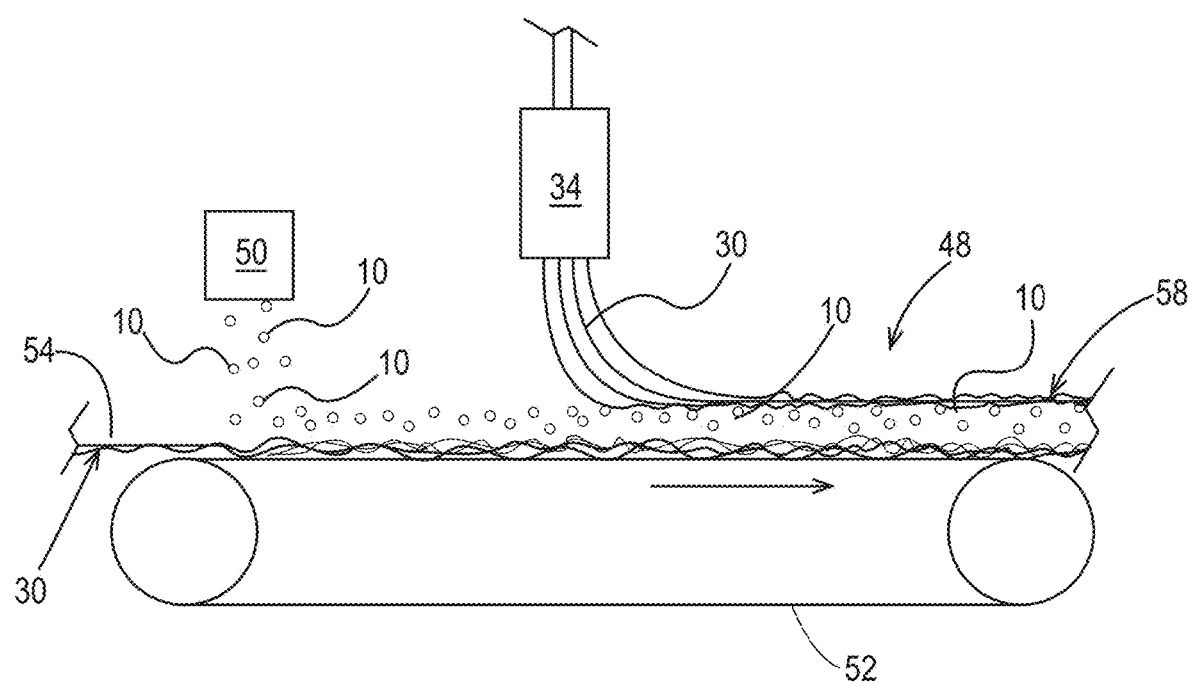
FIG. 8 is a schematic representation of another example of a process for making a fibrous structure according to the present invention.

FIG. 8 illustrates yet another example of a method for making a fibrous structure 48 according to the present invention. The method comprises the steps of forming a first layer 54 of a plurality of fibrous elements 30. One or more matrix particles 10 are deposited onto a surface of the first layer 54, which is carried by a collection belt 52, from a matrix particle source 50. A second layer 58 comprising a plurality of fibrous elements 30 produced from a spinning die 34 are then formed on top of the matrix particles 10 such that the matrix particles 10 are positioned between the first layer 54 and the second layer 58.

In one example, the fibrous structures may independently exhibit any suitable basis weight, for example from about 100 gsm to about 5000 gsm and/or from about 250 gsm to about 3000 gsm and/or from about 500 gsm to about 2000 gsm. In one example, the fibrous elements within the fibrous structures may independently be present in the fibrous structures at any suitable basis weight, for example from about 10 to about 1000 gsm and/or from about 10 gsm to about 500 gsm and/or from about 20 gsm to about 400 gsm and/or from about 100 gsm to about 300 gsm. In one example, the matrix particles, when present within the fibrous structures may independently be present in the fibrous structures at any suitable basis weight, for example from about 10 gsm to about 4000 gsm and/or from about 50 gsm to about 4000 gsm and/or from about 100 gsm to about 4000 gsm and/or from about 250 gsm to about 3000 gsm and/or from about 500 gsm to about 2000 gsm.

In one example, other particles comprising other active agents may be added to the fibrous structures and/or between the fibrous structures. For example, a perfume may be positioned between the two fibrous structures before associating the fibrous structures together. In one example, the fibrous structures of the present invention are void or substantially void (doesn't negatively impact the foam generation by the fibrous structures) of suds suppressing agents and similar active agents that prevent and/or inhibit foam generation.

NON-LIMITING EXAMPLES

Example 1

Matrix Particle Containing Terminal Aminosilicone and Polyvinyl Alcohol

Premix 1: 650 g of distilled water is added to a suitable vessel and stirring with an overhead mixer is initiated. Then 350 g of Selvol 505 Polyvinyl Alcohol (powder), commercially available from Sekisui Chemical, Secaucus, N.J., is added to the distilled water while stirring. After the polyvinyl alcohol has been dispersed thoroughly in the water, the vessel is heated to temperature of 90° C. Stirring and heating at 90° C. continues for approximately 2 hours to fully dissolve the polyvinyl alcohol within the water to create a polyvinyl alcohol solution, wherein the polyvinyl alcohol is a matrix material of the present invention.

Premix 2: 800 g of Silsoft 253, a pre-made terminal aminosilicone emulsion commercially available from Momentive, which contains amodimethicone, emuisfiers (C11-15 pareth 7, laureth 9, glycerin and trideceth 12) and water with a silicone content of 20%.

A spray drying mixture is then made by combining the 1000 g (650 g of distilled water and 350 g of polyvinyl alcohol) of Premix 1 with the 800 g of Premix 2. This spray drying mixture is stirred by an overhead mixer (about 100 rpm with suitable sized impeller) until completely mixed approximately for 1 hour and then 1600 g additional distilled water is added to reduce the viscosity to a viscosity of less than about 1000 cP, the lower the better for better droplet formation, and enable spray drying. The fully formulated reduced viscosity mixture is then stirred for 20 minutes.

The spray drying process is accomplished using a Niro Mobile Minor™ unit having a 1 meter diameter and 2.5 meter height commercially available from GEA Process Engineering Inc., formerly Niro Inc. The spray drying unit is equipped with a rotary atomizer The fully formulated reduced viscosity mixture is pumped in at 40 mL/min. The inlet air temperature is controlled to 200° C. and the outlet temperature is controlled to 100° C. by adjusting heating elements and flowrates. Matrix particles (as shown in FIG. 1) comprising polyvinyl alcohol and terminal aminosilicone are formed by the spray drying process as shown in FIG. 2. These matrix particles may be agglomerated to form an agglomerated particle.

Example 2

Agglomerated Particles 2200 g of matrix particles comprising polyvinyl alcohol and silicone, for example aminosilicone, such as terminal aminosilicone, and 2200 g of matrix particles comprising polyvinyl alcohol and perfume are added to a 6 L Twin Axis Forberg-style Paddle Mixer. The matrix particles are mixed for 30 seconds at a mixer tip speed of 1.43 m/s. A binder consisting of 15% polyvinylpyrrolidone in isopropanol is atomized and sprayed into the matrix particle fluid bed created in the mixer resulting in agglomeration of the matrix particles. The binder is added at a rate of 300 g/min, and atomized using a two fluid nozzle with air as the second fluid. A total of 600 g of binder is added, resulting in delivery of 75 g of polyvinylpyrrolidone. The entire batch of agglomerated particles is then immediately removed from the mixer and dried in a fluid bed dryer to remove the isopropanol. Drying is completed at 60° C. The dry agglomerated particles are then sieved to remove agglomerated particles that are larger than 1180 μm and agglomerates and un-agglomerated fines smaller than 250 μm as measured according to the Median Particle Size Test Method described herein.

Example 4

Matrix Particle Containing Silica and Polyvinyl Alcohol

Premix 1: 650 g of distilled water is added to a suitable vessel and stirring with an overhead mixer is initiated. Then 350 g of Selvol 505 Polyvinyl Alcohol (powder), commercially available from Sekisui Chemical, Secaucus, NJ, is added to the distilled water while stirring. After the polyvinyl alcohol has been dispersed thoroughly in the water, the vessel is heated to temperature of 90° C. Stirring and heating at 90° C. continues for approximately 2 hours to fully dissolve the polyvinyl alcohol within the water to create a polyvinyl alcohol solution, wherein the polyvinyl alcohol is a matrix material of the present invention.

To Premix 1 is added 200 g of silica particles to form a spray drying mixture. This spray drying mixture is stirred by an overhead mixer (about 100 rpm with suitable sized impeller) until completely mixed approximately for 1 hour and then 1600 g additional distilled water is added to reduce the viscosity to a viscosity of less than about 1000 cP, the lower the better for better droplet formation, and enable spray drying. The fully formulated reduced viscosity mixture is then stirred for 20 minutes.

The spray drying process is accomplished using a Niro Mobile Minor™ unit having a 1 meter diameter and 2.5 meter height commercially available from GEA Process Engineering Inc., formerly Niro Inc. The spray drying unit is equipped with a rotary atomizer The fully formulated reduced viscosity mixture is pumped in at 40 mL/min. The inlet air temperature is controlled to 200° C. and the outlet temperature is controlled to 100° C. by adjusting heating elements and flowrates. Matrix particles (as shown in FIG. 1) comprising polyvinyl alcohol and silica particles are formed by the spray drying process as shown in FIG. 2. These matrix particles may be agglomerated to form an agglomerated particle.

Example 4

Fibrous Structure Comprising Matrix Particles and/or Agglomerated Particles

A fibrous structure, for example a water-soluble fibrous structure, comprising a plurality of matrix particles from Example 1 and/or a plurality of agglomerated particles from Example 2 is made as follows.

Fibrous elements may be formed by means of a small-scale apparatus comprising a pressurized tank, suitable for batch operation is filled with a suitable filament-forming composition for spinning A pump, such as a Zenith®, type PEP II, having a capacity of 5.0 cubic centimeters per revolution (cc/rev), manufactured by Parker Hannifin Corporation, Zenith Pumps division, of Sanford, N.C., USA may be used to facilitate transport of the filament-forming composition to a spinning die. The flow of the filament-forming composition from the pressurized tank to the spinning die may be controlled by adjusting the number of revolutions per minute (rpm) of the pump. Pipes are used to connect the pressurized tank, the pump, and the spinning die.

The spinning die has several rows of circular extrusion nozzles (fibrous element-forming holes) spaced from one another at a pitch P of about 1.524 millimeters (about 0.060 inches). The nozzles have individual inner diameters of about 0.305 millimeters (about 0.012 inches) and individual outside diameters of about 0.813 millimeters (about 0.032 inches). Each individual nozzle is encircled by an annular and divergently flared orifice (concentric attenuation fluid hole to supply attenuation air to each individual melt capillary. The filament-forming composition extruded through the nozzles is surrounded and attenuated by generally cylindrical, humidified air streams supplied through the orifices.

Attenuation air can be provided by heating compressed air from a source by an electrical-resistance heater, for example, a heater manufactured by Chromalox, Division of Emerson Electric, of Pittsburgh, Pa., USA. An appropriate quantity of steam was added to saturate or nearly saturate the heated air at the conditions in the electrically heated, thermostatically controlled delivery pipe. Condensate was removed in an electrically heated, thermostatically controlled, separator.

The embryonic fibrous elements are dried by a drying air stream having a temperature from about 149° C. (about 300° F.) to about 315° C. (about 600° F.) by an electrical resistance heater (not shown) supplied through drying nozzles and discharged at an angle of about 90 degrees relative to the general orientation of the non-thermoplastic embryonic fibers being extruded. The dried embryonic fibrous elements are collected on a collection device, such as, for example, a movable foraminous belt or patterned collection belt. The addition of a vacuum source directly under the formation zone may be used to aid collection of the fibers.

A particle source, for example a matrix particle source such as a feeder, suitable to supply a flow of particles, for example matrix particles and/or agglomerated particles according to the present invention, is placed directly above the drying region for the fibrous elements. For example, a vibratory feeder made by Retsch® of Haan, Germany can be used as the particle source. In order to aid in a consistent distribution of particles in the cross direction the particles are fed onto a tray that started off the width of the feeder and ended at the same width as the spinning die face to ensure particles were delivered into all areas of fibrous element formation. The tray is completely enclosed with the exception of the exit to minimize disruption of the particle feed.

While embryonic fibrous elements are being formed, the feeder is turned on and particles are introduced into the fibrous element stream. In this case, Green Zero (Green Speckle Granules) manufactured by Genencor International® of Leiden, The Netherlands is used as the particles. The particles associated and/or mixed with the fibrous elements and are collected together on the collection belt to form a fibrous structure according to the present invention.

Test Methods

Unless otherwise specified, all tests described herein including those described under the Definitions section and the following test methods are conducted on samples that have been conditioned in a conditioned room at a temperature of 23° C.±1.0° C. and a relative humidity of 50%±2% for a minimum of 2 hours prior to the test. The samples tested are "usable units." "Usable units" as used herein means articles, for example unit dose articles/products, used by consumers for their intended purpose. All tests are conducted under the same environmental conditions and in such conditioned room. Do not test samples that have defects such as wrinkles, tears and like. Samples conditioned as described herein are considered dry samples (such as "dry filaments") for testing purposes. All instruments are calibrated according to manufacturer's specifications.

Basis Weight Test Method

Basis weight is defined as the weight in g/m² of a sample being tested. It is determined by accurately weighing a known area of a conditioned sample using an appropriate balance, recording the weight and area of sample tested, applying the appropriate conversion factors, and finally calculating the basis weight in g/m² of the sample.

Basis weight is measured by cutting a sample from a single web, a stack of webs, or other appropriate plied up, or consumer salable unit and weighing the sample using a top loading analytical balance with a resolution of ±0.001 g. The sample must be equilibrated at a temperature of 73°±2° F. (23°±1° C.) and a relative humidity of 50% (±2%) for a minimum of two hours prior to cutting samples. During weighing, the balance is protected from air drafts and other disturbances using a draft shield. A precision cutting die, measuring 1.625×1.625 in (41.275×41.275 mm) is used to prepare all samples. Select usable sample areas which are clean, free of holes, tears, wrinkles and other defects.

For each sample use the die cutter described above to cut a sample, weigh the mass of the sample, and record the mass result to the nearest 0.001 g.

The Basis Weight is calculated in g/m² as follows:

Basis Weight=(Mass of sample)/(Area of sample).

Or specifically,

Basis Weight (g/m²)=(Mass of sample (g))/(0.001704 m²).

Report result to the nearest 0.1 g/m². Sample dimensions can be changed or varied using a similar precision cutter as mentioned above. If the sample dimension is decreased, then several samples should be measured and the mean value reported as its basis weight.

Median Particle Size Test Method

This test method must be used to determine size of matrix particles as well as agglomerated particles.

The median particle size test is conducted to determine the median particle size of the matrix particle using ASTM D 502-89, "Standard Test Method for Particle Size of Soaps and Other Detergents", approved May 26, 1989, with a further specification for sieve sizes used in the analysis. Following section 7, "Procedure using machine-sieving method," a nest of clean dry sieves containing U.S. Standard (ASTM E 11) sieves #8 (2360 µm), #12 (1700 µm), #16 (1180 µm), #20 (850 µm), #30 (600 µm), #40 (425 µm), #50 (300 µm), #70 (212 µm), #100 (150 µm) is required. The prescribed Machine-Sieving Method is used with the above sieve nest. The matrix particle is used as the sample. A suitable sieve-shaking machine can be obtained from W.S. Tyler Company of Mentor, Ohio, U.S.A.

The data are plotted on a semi-log plot with the micron size opening of each sieve plotted against the logarithmic abscissa and the cumulative mass percent ($Q_3$) plotted against the linear ordinate. An example of the above data representation is given in ISO 9276-1:1998, "Representation of results of particle size analysis—Part 1: Graphical Representation", FIG. A.4. The matrix particle median particle size ($D_{50}$), for the purpose of this invention, is defined as the abscissa value at the point where the cumulative mass percent is equal to 50 percent, and is calculated by a straight line interpolation between the data points directly above (a50) and below (b50) the 50% value using the following equation:

$$D_{50}=10^{\wedge}[\text{Log}(D_{a50})-(\text{Log}(D_{a50})-\text{Log}(D_{b50}))*(Q_{a50}-50\%)/(Q_{a50}-Q_{b50})]$$

where $Q_{a50}$ and $Q_{b50}$ are the cumulative mass percentile values of the data immediately above and below the 50$^{th}$ percentile, respectively; and $D_{a50}$ and $D_{b50}$ are the micron sieve size values corresponding to these data.

In the event that the 50$^{th}$ percentile value falls below the finest sieve size (150 µm) or above the coarsest sieve size (2360 µm), then additional sieves must be added to the nest following a geometric progression of not greater than 1.5, until the median falls between two measured sieve sizes.

The Distribution Span of the Matrix Particle is a measure of the breadth of the matrix particle size distribution about the median. It is calculated according to the following:

$$Span=(D_{84}/D_{50}+D_{50}/D_{16})/2$$

Where $D_{50}$ is the median particle size and $D_{84}$ and $D_{16}$ are the particle sizes at the sixteenth and eighty-fourth percentiles on the cumulative mass percent retained plot, respectively.

In the event that the $D_{16}$ value falls below the finest sieve size (150 μm), then the span is calculated according to the following:

$$Span=(D_{84}/D_{50}).$$

In the event that the $D_{84}$ value falls above the coarsest sieve size (2360 μm), then the span is calculated according to the following:

$$Span=(D_{50}/D_{16}).$$

In the event that the $D_{16}$ value falls below the finest sieve size (150 μm) and the $D_{84}$ value falls above the coarsest sieve size (2360 μm), then the distribution span is taken to be a maximum value of 5.7.

Analysis of Free Perfume in Matrix Particles

This method is suitable for measuring leakage and/or diffusion or lack thereof of a hydrophobic active agent, in this case one or more perfumes.

All laboratory instruments should be operated according to manufacturers' instructions, as set forth in the instrument operation manuals and instructional materials, unless otherwise indicated.

Apparatus
1. Laboratory Timer.
2. HT Tuffy® membrane filter, Schwartz, Twin Rivers, WI., USA
3. Gas Chromatograph (GC): Agilent model 6890 or equivalent
4. GC column: Agilent DB-5MS, 30 M×0.250 mm ID, 1.0 μm film thickness obtained from Agilent Technologies, Inc. Wilmington, DE., USA.
5. Carrier gas, helium, 1.2 ml/min. flow rate.
6. The Detector is a model Agilent 5973 Mass Selective Detector (or equivalent) obtained from Agilent Technologies, Inc., Wilmington, DE, USA having a source temperature of about 230° C., and a MS Quad temperature of about 150° C.

Sample Preparation
7. After storing the particles at 40° C. overnight, place 0.2 g of perfume particles into the bottom of a 20 mL glass vial (minimizing product on sides or top of vial).
8. To this vial add 10 mL of hexane.
9. Using a touch vortexing unit, vortex sample for 10 seconds (if large amounts of product are still agglomerated to the bottom, vortex for another 10 seconds).
10. Then mix using a roller mixer for 5 minutes.
11. Using a syringe and nylon syringe filter with a 0.45 μm HT Tuffy® Membrane filter (if it is clear, no filter needed) 1.5 mL of the clear hexane layer into a 2 mL GC vial. Cap vial tightly.
12. A 2 μL aliquot of each sample will then be analyzed by GC/MS.
13. All samples are analyzed in triplicate (n=2).

Analysis
1. Transfer sample vials to proper sample tray and proceed with GC-MS analysis.
2. Start sequence of sample loading and analysis. In this step, the GC-MS analysis run is in split mode with split ratio 10:1. The following temperature program is used:
   an initial temperature of about 75° C.
   increase the initial temperature at a rate of about 6° C./min until a temperature of 280° C. is reached, then hold for 3.83 minutes. The total run time is 38 minutes.
3. Perfume compounds are identified using the MS spectral libraries of John Wiley & Sons (Wiley 10) and the National Institute of Standards and Technology (NIST 08), purchased and licensed through Agilent Technologies, Inc., Wilmington, DE., USA.
4. Chromatographic peaks for specific ions are integrated using the Chemstation software (version E) obtained from Agilent Technologies, Inc., Wilmington, DE., USA.
5. Use the perfume standard and prepare it according to the method described herein and perform the GC-MS analysis, analyze the peaks, and integrate using the Chemstation software, as described herein.
6. Construct a calibration curve using peak area vs. known amount of the perfume to obtain a linear curve.
7. Calculate the corresponding perfume amount from the peak area of the hexane extracted free perfume from the test sample by using the linear.
8. The percent of free oil in the test sample is the amount of the free perfume (from Step 7) over the total perfume in the sample (encapsulated amount).

Water Content Test Method

The water (moisture) content present in a fibrous element and/or particle and/or fibrous structure is measured using the following Water Content Test Method. A fibrous element and/or particle and/or fibrous structure or portion thereof ("sample") in the form of a pre-cut sheet is placed in a conditioned room at a temperature of 23° C.±1.0° C. and a relative humidity of 50%±2% for at least 24 hours prior to testing. Each fibrous structure sample has an area of at least 4 square inches, but small enough in size to fit appropriately on the balance weighing plate. Under the temperature and humidity conditions mentioned above, using a balance with at least four decimal places, the weight of the sample is recorded every five minutes until a change of less than 0.5% of previous weight is detected during a 10 minute period. The final weight is recorded as the "equilibrium weight". Within 10 minutes, the samples are placed into the forced air oven on top of foil for 24 hours at 70° C.±2° C. at a relative humidity of 4%±2% for drying. After the 24 hours of drying, the sample is removed and weighed within 15 seconds. This weight is designated as the "dry weight" of the sample.

The water (moisture) content of the sample is calculated as follows:

$$\% \text{ Water in sample} = 100\% \times \frac{(\text{Equilibrium weight of sample} - \text{Dry weight of sample})}{\text{Dry weight of sample}}$$

The % Water (moisture) in sample for 3 replicates is averaged to give the reported % Water (moisture) in sample. Report results to the nearest 0.1%.

Diameter Test Method

The diameter of a discrete fibrous element or a fibrous element within a fibrous structure is determined by using a Scanning Electron Microscope (SEM) or an Optical Microscope and an image analysis software. A magnification of 200 to 10,000 times is chosen such that the fibrous elements are suitably enlarged for measurement. When using the SEM, the samples are sputtered with gold or a palladium compound to avoid electric charging and vibrations of the fibrous element in the electron beam. A manual procedure for determining the fibrous element diameters is used from the image (on monitor screen) taken with the SEM or the optical microscope. Using a mouse and a cursor tool, the edge of a randomly selected fibrous element is sought and then measured across its width (i.e., perpendicular to fibrous element direction at that point) to the other edge of the fibrous element. A scaled and calibrated image analysis tool provides the scaling to get actual reading in um. For fibrous elements within a fibrous structure, several fibrous element are randomly selected across the sample of the fibrous structure using the SEM or the optical microscope. At least two portions of the fibrous structure are cut and tested in this manner. Altogether at least 100 such measurements are made and then all data are recorded for statistical analysis. The recorded data are used to calculate average (mean) of the fibrous element diameters, standard deviation of the fibrous element diameters, and median of the fibrous element diameters.

Another useful statistic is the calculation of the amount of the population of fibrous elements that is below a certain upper limit. To determine this statistic, the software is programmed to count how many results of the fibrous element diameters are below an upper limit and that count (divided by total number of data and multiplied by 100%) is reported in percent as percent below the upper limit, such as percent below 1 micrometer diameter or %-submicron, for example. We denote the measured diameter (in μm) of an individual circular fibrous element as di.

In the case that the fibrous elements have non-circular cross-sections, the measurement of the fibrous element diameter is determined as and set equal to the hydraulic diameter which is four times the cross-sectional area of the fibrous element divided by the perimeter of the cross-section of the fibrous element (outer perimeter in case of hollow fibrous elements). The number-average diameter, alternatively average diameter is calculated as:

$$d_{num} = \frac{\sum_{i=1}^{n} d_i}{n}$$

Weight Average Molecular Weight Test Method

The weight average molecular weight (Mw) of a material, such as a polymer, is determined by Gel Permeation Chromatography (GPC) using a mixed bed column. A high performance liquid chromatograph (HPLC) having the following components: Millenium®, Model 600E pump, system controller and controller software Version 3.2, Model 717 Plus autosampler and CHM-009246 column heater, all manufactured by Waters Corporation of Milford, MA, USA, is utilized. The column is a PL gel 20 μm Mixed A column (gel molecular weight ranges from 1,000 g/mol to 40,000,000 g/mol) having a length of 600 mm and an internal diameter of 7.5 mm and the guard column is a PL gel 20 μm, 50 mm length, 7.5 mm ID. The column temperature is 55° C. and the injection volume is 200 μL. The detector is a DAWN® Enhanced Optical System (EOS) including Astra® software, Version 4.73.04 detector software, manufactured by Wyatt Technology of Santa Barbara, CA, USA, laser-light scattering detector with K5 cell and 690 nm laser. Gain on odd numbered detectors set at 101. Gain on even numbered detectors set to 20.9. Wyatt Technology's Optilab® differential refractometer set at 50° C. Gain set at 10. The mobile phase is HPLC grade dimethylsulfoxide with 0.1% w/v LiBr and the mobile phase flow rate is 1 ml/min, isocratic. The run time is 30 minutes.

A sample is prepared by dissolving the material in the mobile phase at nominally 3 mg of material/1 mL of mobile phase. The sample is capped and then stirred for about 5 minutes using a magnetic stirrer. The sample is then placed in an 85° C. convection oven for 60 minutes. The sample is then allowed to cool undisturbed to room temperature. The sample is then filtered through a 5 μm Nylon membrane, type Spartan-25, manufactured by Schleicher & Schuell, of Keene, NH, USA, into a 5 milliliter (mL) autosampler vial using a 5 mL syringe.

For each series of samples measured (3 or more samples of a material), a blank sample of solvent is injected onto the column. Then a check sample is prepared in a manner similar to that related to the samples described above. The check sample comprises 2 mg/mL of pullulan (Polymer Laboratories) having a weight average molecular weight of 47,300 g/mol. The check sample is analyzed prior to analyzing each set of samples. Tests on the blank sample, check sample, and material test samples are run in duplicate. The final run is a run of the blank sample. The light scattering detector and differential refractometer is run in accordance with the "Dawn EOS Light Scattering Instrument Hardware Manual" and "Optilab® DSP Interferometric Refractometer Hardware Manual," both manufactured by Wyatt Technology Corp., of Santa Barbara, CA, USA, and both incorporated herein by reference.

The weight average molecular weight of the sample is calculated using the detector software. A dn/dc (differential change of refractive index with concentration) value of 0.066 is used. The baselines for laser light detectors and the refractive index detector are corrected to remove the contributions from the detector dark current and solvent scattering. If a laser light detector signal is saturated or shows excessive noise, it is not used in the calculation of the molecular mass. The regions for the molecular weight characterization are selected such that both the signals for the 90° detector for the laser-light scattering and refractive index are greater than 3 times their respective baseline noise levels. Typically, the high molecular weight side of the chromatogram is limited by the refractive index signal and the low molecular weight side is limited by the laser light signal.

The weight average molecular weight can be calculated using a "first order Zimm plot" as defined in the detector software. If the weight average molecular weight of the sample is greater than 1,000,000 g/mol, both the first and second order Zimm plots are calculated, and the result with the least error from a regression fit is used to calculate the molecular mass. The reported weight average molecular weight is the average of the two runs of the material test sample.

Thickness Test Method

Thickness of a fibrous structure is measured by cutting 5 samples of a fibrous structure sample such that each cut sample is larger in size than a load foot loading surface of a VIR Electronic Thickness Tester Model II available from Thwing-Albert Instrument Company, Philadelphia, PA. Typically, the load foot loading surface has a circular surface area of about 3.14 in². The sample is confined between a horizontal flat surface and the load foot loading surface. The load foot loading surface applies a confining pressure to the sample of 15.5 g/cm². The thickness of each sample is the resulting gap between the flat surface and the load foot loading surface. The thickness is calculated as the average thickness of the five samples. The result is reported in millimeters (mm).

Shear Viscosity Test Method

The shear viscosity of a filament-forming composition of the present invention is measured using a capillary rheometer, Goettfert Rheograph 6000, manufactured by Goettfert USA of Rock Hill SC, USA. The measurements are conducted using a capillary die having a diameter D of 1.0 mm and a length L of 30 mm (i.e., L/D=30). The die is attached to the lower end of the rheometer's 20 mm barrel, which is held at a die test temperature of 75° C. A preheated to die test temperature, 60 g sample of the filament-forming composition is loaded into the barrel section of the rheometer. Rid the sample of any entrapped air. Push the sample from the barrel through the capillary die at a set of chosen rates 1,000-10,000 seconds$^{-1}$. An apparent shear viscosity can be calculated with the rheometer's software from the pressure drop the sample experiences as it goes from the barrel through the capillary die and the flow rate of the sample through the capillary die. The log (apparent shear viscosity) can be plotted against log (shear rate) and the plot can be fitted by the power law, according to the formula $\eta=K\gamma^{n-1}$, wherein K is the material's viscosity constant, n is the material's thinning index and $\gamma$ is the shear rate. The reported apparent shear viscosity of the filament-forming composition herein is calculated from an interpolation to a shear rate of 3,000 sec$^{-1}$ using the power law relation.

Fibrous Element Composition Test Method

In order to prepare fibrous elements for fibrous element composition measurement, the fibrous elements must be conditioned by removing any coating compositions and/or materials present on the external surfaces of the fibrous elements that are removable. An example of a method for doing so is washing the fibrous elements 3 times with a suitable solvent that will remove the external coating while leaving the fibrous elements unaltered. The fibrous elements are then air dried at 23° C.±1.0° C. until the fibrous elements comprise less than 10% moisture. A chemical analysis of the conditioned fibrous elements is then completed to determine the compositional make-up of the fibrous elements with respect to the filament-forming materials and the active agents and the level of the filament-forming materials and active agents present in the fibrous elements.

The compositional make-up of the fibrous elements with respect to the filament-forming material and the active agents can also be determined by completing a cross-section analysis using TOF-SIMs or SEM. Still another method for determining compositional make-up of the fibrous elements uses a fluorescent dye as a marker. In addition, as always, a manufacturer of fibrous elements should know the compositions of their fibrous elements.

Dissolution Test Method

Figure 11:
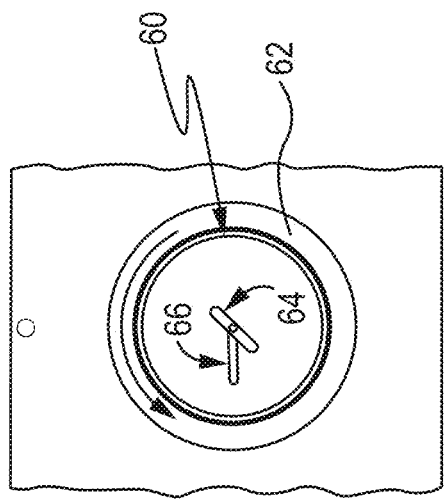
FIG. 11 is a schematic representation of a top view of FIG. 10.
Figure 10:
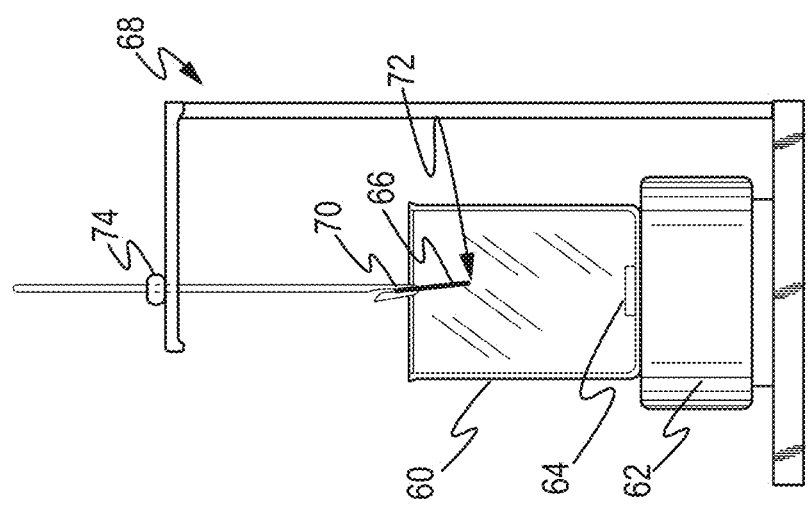
FIG. 10 is a schematic representation of FIG. 9 during the operation of the dissolution test.
Figure 9:
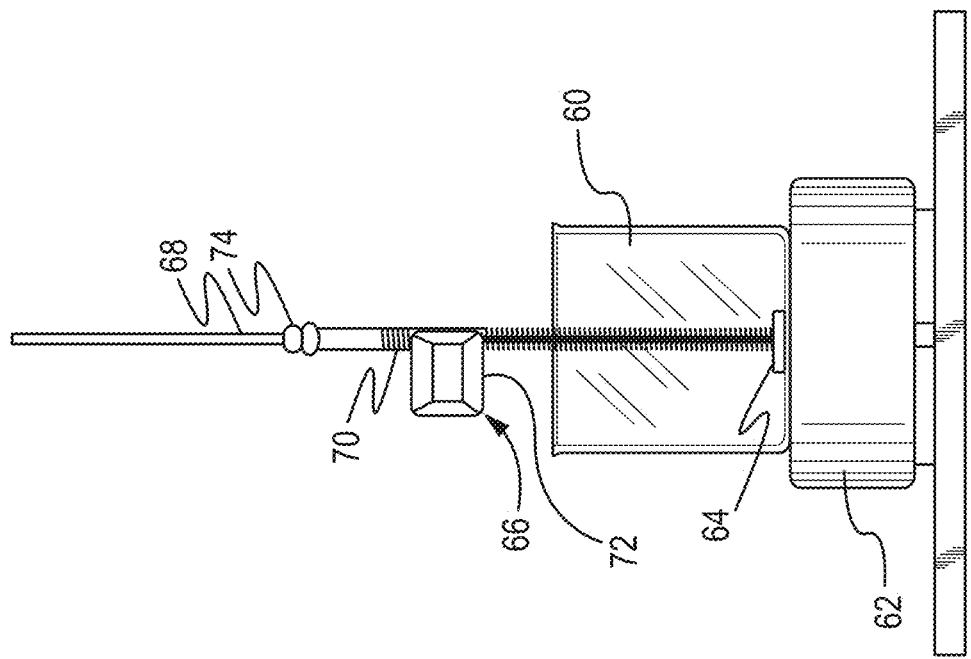
FIG. 9 is a schematic representation of an example of a setup of equipment used in measuring dissolution according to the present invention.

Apparatus and Materials (also, see FIGS. 9 through 11):
600 mL Beaker 60
Magnetic Stirrer 62 (Labline Model No. 1250 or equivalent)
Magnetic Stirring Rod 64 (5 cm)
Thermometer (1 to 100° C.+/−1° C.)
Cutting Die—Stainless Steel cutting die with dimensions 3.8 cm×3.2 cm
Timer (0-3,600 seconds or 1 hour), accurate to the nearest second. Timer used should have sufficient total time measurement range if sample exhibits dissolution time greater than 3,600 seconds. However, timer needs to be accurate to the nearest second.

Polaroid 35 mm Slide Mount 66 (commercially available from Polaroid Corporation or equivalent)
35 mm Slide Mount Holder 68 (or equivalent)
City of Cincinnati Water or equivalent having the following properties: Total Hardness=155 mg/L as $CaCO_3$; Calcium content=33.2 mg/L; Magnesium content=17.5 mg/L; Phosphate content=0.0462.

Test Protocol

Equilibrate samples in constant temperature and humidity environment of 23° C.±1.0° C. and 50% RH±2% for at least 2 hours. Measure the basis weight of the fibrous structure sample to be measured using Basis Weight Test Method defined herein. Cut three dissolution test specimens from the fibrous structure sample using cutting die (3.8 cm×3.2 cm), so it fits within the 35 mm Slide Mount 66, which has an open area dimensions 24×36 mm. Lock each specimen in a separate 35 mm slide mount 66. Place magnetic stirring rod 64 into the 600 mL beaker 60. Turn on the city water tap flow (or equivalent) and measure water temperature with thermometer and, if necessary, adjust the hot or cold water to maintain it at the testing temperature. Testing temperature is 15° C.±1° C. water. Once at testing temperature, fill beaker 60 with 500 mL±5 mL of the 15° C.±1° C. city water. Place full beaker 60 on magnetic stirrer 62, turn on stirrer 64, and adjust stir speed until a vortex develops and the bottom of the vortex is at the 400 mL mark on the beaker 60. Secure the 35 mm slide mount 66 in the alligator clamp 70 of the 35 mm slide mount holder 68 such that the long end 72 of the slide mount 66 is parallel to the water surface. The alligator clamp 70 should be positioned in the middle of the long end 72 of the slide mount 66. The depth adjuster 74 of the holder 68 should be set so that the distance between the bottom of the depth adjuster 74 and the bottom of the alligator clip 70 is ~11+/31 0.125 inches. This set up will position the sample surface perpendicular to the flow of the water. In one motion, drop the secured slide and clamp into the water and start the timer. The sample is dropped so that the sample is centered in the beaker. Disintegration occurs when the nonwoven structure breaks apart. Record this as the disintegration time. When all of the visible nonwoven structure is released from the slide mount, raise the slide out of the water while continuing the monitor the solution for undissolved nonwoven structure fragments. Dissolution occurs when all nonwoven structure fragments are no longer visible. Record this as the dissolution time.

Three replicates of each sample are run and the average disintegration and dissolution times are recorded. Average disintegration and dissolution times are in units of seconds.

The average disintegration and dissolution times are normalized for basis weight by dividing each by the sample basis weight as determined by the Basis Weight Method defined herein. Basis weight normalized disintegration and dissolution times are in units of seconds/gsm of sample $(s/(g/m^2))$.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A matrix particle comprises one or more uncross-linked matrix materials derived from a water-soluble polymer exhibiting a weight average molecular weight of at least 40,000 g/mol to about 40,000,000 g/mol, wherein the water-soluble polymer is selected from the group consisting of: polyvinyl alcohol, polysaccharides, gums, gelatin, dextrins, polyethylene glycols, gum arabic, larch, pectin, tragacanth, locust bean, guar, alginates, carrageenans, cellulose gums, karaya, polyacrylic acid, polyvinylpyrrolidone, polyacrylamide, and mixtures thereof and one or more hydrophobic active agents comprising a silicone and a perfume;
   wherein the matrix particle comprises one or more pores;
   wherein the silicone and perfume are present in the one or more pores;
   wherein the matrix particle exhibits a perfume leakage of less than or equal to 20% according to the Analysis of Free Perfume in Perfume Matrix Particles described herein.

2. The matrix particle according to claim 1 wherein at least one of the one or more hydrophobic active agents is released from the matrix particle upon the matrix particle contacting water.

3. The matrix particle according to claim 1 wherein at least one of the one or more matrix materials is derived from a polymer selected from the group consisting of:
   polyvinyl alcohol, polysaccharides, and mixtures thereof.

4. The matrix particle according to claim 1 wherein at least one of the one or more matrix materials is derived from polyvinyl alcohol.

5. The matrix particle according to claim 1 wherein the matrix particle comprises from about 10% to about 90% by weight of the one or more matrix materials.

6. The matrix particle according to claim 1 wherein the one or more hydrophobic active agents comprises silicone and at least one hydrophobic active agent selected from the group consisting of: perfumes, essential oils, oils, vitamin oils, vegetable oils, shea butter, cocoa butter, petrolatum, grapeseed oil, sunflower oil, olive oil, argan oil, Vitamin E, and mixtures thereof.

7. The matrix particle according to claim 1 wherein the matrix particle comprises two or more hydrophobic active agents.

8. The matrix particle according to claim 1 wherein the matrix particle exhibits a size of less than 500 µm as measured according to the Median Particle Size Test Method.

9. The matrix particle according to claim 1 wherein at least one of the one or more hydrophobic active agents is in the form of a droplet.

10. The matrix particle according to claim 9 wherein the droplet exhibits a droplet size of at least 0.02 µm to about 200 µm.

11. The matrix particle according to claim 1 wherein at least one of the one or more hydrophobic active agents is a hydrophobic active agent particle.

12. An agglomerated particle comprising a plurality matrix particles according to claim 1.

13. A fibrous structure comprising a plurality of fibrous elements and one or more agglomerated particles according to claim 12.

14. A fibrous structure comprising a plurality of fibrous elements and one or more matrix particles according to claim 1.

15. The matrix particle according to claim 1 wherein the silicone comprises an aminosilicone.

16. The matrix particle according to claim 1 wherein at least one of the one or more matrix materials is derived from a polysaccharide.

17. The matrix particle according to claim 16 wherein the polysaccharide is selected from the group consisting of: starch, starch derivatives, carboxymethylcellulose, hydroxypropyl cellulose, hydroxyethyl cellulose, hydroxypropylmethyl cellulose, methyl cellulose, and mixtures thereof.

* * * * *